(12) United States Patent
Blizzard et al.

(10) Patent No.: US 6,265,395 B1
(45) Date of Patent: *Jul. 24, 2001

(54) CARBAPENEM ANTIBACTERIAL COMPOUNDS, COMPOSITIONS CONTAINING SUCH COMPOUNDS AND METHODS OF TREATMENT

(75) Inventors: Timothy A. Blizzard, Middletown; Ronald W. Ratcliffe, Matawan, both of NJ (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/338,638

(22) Filed: Jun. 23, 1999

Related U.S. Application Data

(60) Provisional application No. 60/090,612, filed on Jun. 25, 1998.

(51) Int. Cl.[7] .................... C07D 477/14; C07D 519/06; A61P 31/04; A61K 31/5415
(52) U.S. Cl. ........................ 514/210.09; 540/302
(58) Field of Search ............................. 540/302; 514/210

(56) References Cited

U.S. PATENT DOCUMENTS

| 4,309,438 | 1/1982 | Christensen et al. | 424/274 |
| 4,479,947 | 10/1984 | Christensen | 424/203 |
| 5,756,725 | * 5/1998 | Wilkening | 540/302 |

FOREIGN PATENT DOCUMENTS

| 0 007 614 | 2/1980 | (EP) . |
| 0 072 014 | 2/1983 | (EP) . |

* cited by examiner

*Primary Examiner*—Mark L. Berch
(74) *Attorney, Agent, or Firm*—Sylvia A. Ayler; Mark R. Daniel

(57) ABSTRACT

Compounds of formula I:

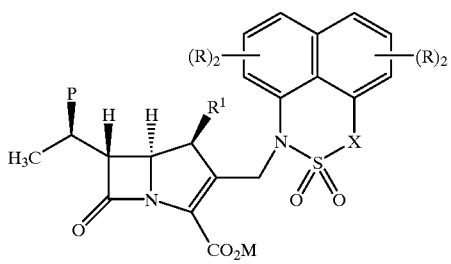

I as well as pharmaceutically acceptable salts thereof useful as carbapenem antibacterial agents are disclosed.

16 Claims, No Drawings

CARBAPENEM ANTIBACTERIAL COMPOUNDS, COMPOSITIONS CONTAINING SUCH COMPOUNDS AND METHODS OF TREATMENT

This application claims the benefit of U.S. Provisional Application No. 60/090,612, filed Jun. 25, 1998.

BACKGROUND OF THE INVENTION

The present invention relates to carbapenem antibacterial agents in which the carbapenem nucleus is substituted at the 2-position with a 2,2 dioxo-3-X-2-thia-1-aza-phenalene, linked through a $CH_2$ group, where X is a carbon, nitrogen, or oxygen atom.

The carbapenems of the present invention are useful against gram positive microorganisms, especially methicillin resistant Staphylococcus aureus (MRSA), methicillin resistant Staphylococcus epidermidis (MRSE), and methicillin resistant coagulase negative Staphylococci (MRCNS). The antibacterial compounds of the present invention thus comprise an important contribution to therapy for treating infections caused by these difficult to control pathogens. There is an increasing need for agents effective against such pathogens (MRSA/MRCNS) which are at the same time relatively free from undesirable side effects.

SUMMARY OF THE INVENTION

The compounds of the invention are represented by formula I:

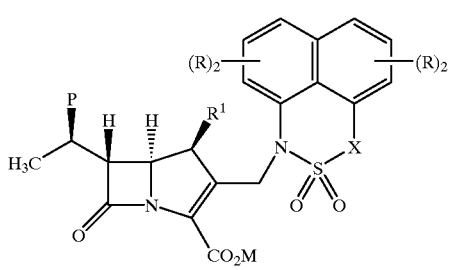

I including pharmaceutically acceptable salts thereof, wherein:

$R^1$ represents H or methyl;

$CO_2M$ represents a carboxylic acid, a pharmaceutically acceptable carboxylic acid salt, carboxylate anion, a pharmaceutically acceptable ester group or a carboxylic acid protected by a protecting group;

X represents $CR^2R^3$, $NR^2$ or O;

$R^2$ and $R^3$, independently represent H or $C_{1-6}$ alkyl, or $R^2$ and $R^3$ together with the core carbon atom in the group $CR^2R^3$ form a 3–6 membered cycloalkyl ring;

P represents hydrogen, hydroxyl, F or hydroxyl protected by a hydroxyl-protecting group;

Each R independently represents $R^b$,

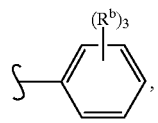

,

—Het($R^b$)$_3$, $C_{2-6}$ alkenyl, or a group L—Q—$R^q$ with the proviso that only one R group of the type L—Q—$R^q$ can be present or one R group may be taken with L, if present, and any intervening atoms to represent a 5–6 membered ring;

L is $C_{1-4}$ straight or branched alkylene, uninterrupted, interrupted or terminated by 1–2 of O, S, $NR^a$, C(O), $CO_2$ and C(O)$NR^a$;

Q represents:

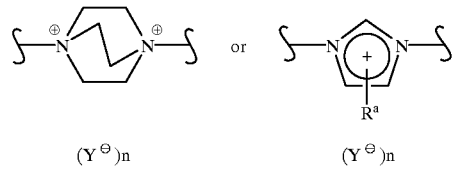

$Y^-$ is a charge balancing group;

n is a value from 0 to 2 selected to maintain overall charge neutrality;

$R^a$ is H or $C_{1-6}$ alkyl;

$R^q$ is $C_{1-6}$ alkyl, straight or branched, uninterrupted, interrupted or terminated by 1–2 of O, S, $NR^a$, C(O), C(O)O, C(O)$NR^a$, —CH=CH—, —Het($R^b$)$_3$—, —C(O)Het($R^b$)$_3$—, —C(O)$NR^a$Het($R^b$)$_3$—,

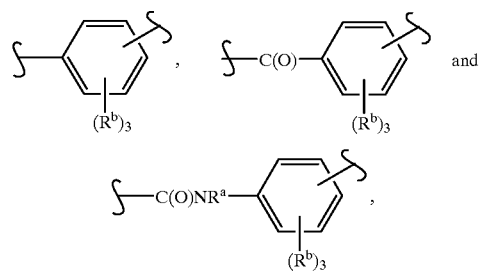

said $R^q$ being unsubstituted or substituted with 1–3 $R^c$ groups;

Het is a heteroaryl group;

each $R^b$ is independently selected from H, halo, $OR^a$, OC(O)$R^a$, C(O)$R^a$, CN, C(O)$NR^aR^d$, $NO_2$, $NR^aR^d$, $SO_2NR^aR^d$ and $C_{1-4}$ alkyl unsubstituted or substituted with 1–3 groups selected from $R^e$;

each $R^c$ is independently selected from halo, $OR^f$, OC(O)$R^f$, $SR^f$, S(O)$R^f$, $SO_2R^f$, CN, C(O)$R^f$, $CO_2R^f$, $NR^fR^g$, $N^+R^aR^fR^gZ^-$, C(O)$NR^aR^f$, —Het($R^b$)$_3$, C(=$N^+R^aR^f$)$R^aZ^-$, C(=$N+R^aR^f$)$NR^aR^fZ^-$, $NR^aC$(=$N^+R^aR^f$)$R^aZ^-$, $NR^aC$(=$N^+R^aR^f$)$NR^aR^fZ^-$, heteroarylium($R^b$)$_3Z^-$, $SO_2NR^aR^f$, OC(O)$NR^aR^f$, $NR^aC$(O)$R^f$, $NR^aC$(O)$NR^aR^f$, and

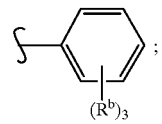

;

or in the alternative, when 2 or more $R^c$ groups are present, 2 $R^c$ groups may be taken together with any intervening atoms to form a 3–6 membered carbocyclic ring, optionally interrupted with 1–3 of O, S, $NR^g$, and C(O), said ring being unsubstituted or substituted with 1–3 $R^e$ groups;

$R^d$ is H or $C_{1-4}$ alkyl, or $R^a$ and $R^d$ taken together with any intervening atoms represent a 4–6 membered ring;

$R^e$ is selected from halo, $OR^a$, $NR^aR^d$ and $CONR^aR^d$;

$R^f$ is H; $C_{1-6}$ straight or branched chain alkyl, unsubstituted or substituted with 1–3 $R^e$ groups; —Het($R^b$)$_3$; $C_{3-6}$ cycloalkyl, unsubstituted or substituted with 1–3 $R^e$ groups, and

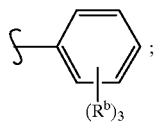

or $R^a$ and $R^f$ together with an intervening atoms form a 4–6 membered ring, optionally interrupted by O, S, $NR^a$ or C(O); and $R^g$ is H, $C_{1-6}$ alkyl, unsubstituted or substituted with 1–3 $R^e$ groups; $C_{3-6}$ cycloalkyl, unsubstituted or substituted with 1–3 $R^e$ groups; $C(=N^+R^aR^f)R^aZ^-$ or $C(=N^+R^aR^f)NR^aR^fZ^-$, or $R^f$ and $R^g$ together with any intervening atoms form a 4–6 membered ring optionally interrupted by O, S, $NR^a$ or C(O); and $Z^-$ is a charge balancing group selected from $Y^-$, a monovalent anion such as acetate, benzoate, bromide, chloride or the like, or an internal anion such as $CO_2M$, where M is a negative charge.

DETAILED DESCRIPTION OF THE INVENTION

The invention is described herein in detail using the terms defined below unless otherwise specified.

Carboxylate anion refers to a negatively charged group —COO—.

The term "alkyl" refers to a monovalent alkane (hydrocarbon) derived radical containing from 1 to 15 carbon atoms unless otherwise defined. It may be straight or branched. Preferred alkyl groups include methyl, ethyl, propyl, isopropyl, butyl and t-butyl. When substituted, alkyl groups may be substituted with up to 3 substituent groups, selected from $R^c$ or $R^e$ as defined, at any available point of attachment. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused. Preferred cycloalkyl groups are cyclopropyl, cyclobutyl, cyclopentyl and cyclohexyl. When substituted, cycloalkyl groups may be substituted with up to 3 substituents selected from $R^c$ or $R^e$ as defined.

A $C_{1-4}$ alkylene group refers to an alkyl group which is attached through two bonds to two different atoms or substituents. The two bonds on the alkylene group can be on the same carbon atom or on different carbon atoms. See, e.g., the following:

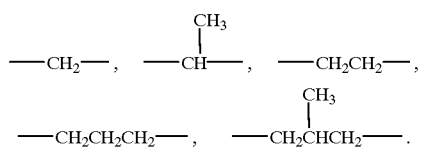

The term "alkenyl" refers to a hydrocarbon radical straight, branched or cyclic containing from 2 to 10 carbon atoms and at least one carbon to carbon double bond.

Preferred alkenyl groups include ethenyl, propenyl, butenyl and cyclohexenyl.

The term "alkynyl" refers to a hydrocarbon radical straight or branched, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms. The preferred aryl groups are phenyl, naphthyl and phenanthrenyl. Aryl groups may likewise be substituted as defined. Preferred substituted aryls include phenyl and naphthyl.

The term "heteroaryl" (Het) refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole. Examples include the following:

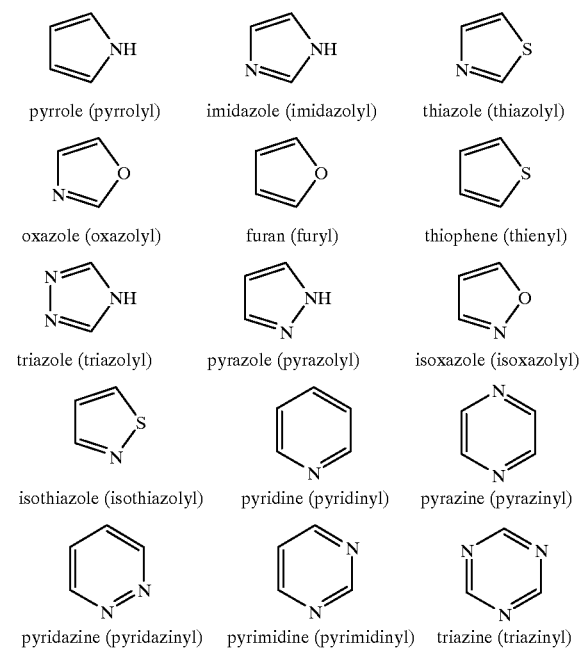

The group L—Q—$R^q$, if present, is attached to either of the two phenyl rings of the 2,2-dioxo-1H,3H-2-thia-1-aza-phenalene, 2,2-dioxo-1H,3H-2-thia-1,3-diaza-phenalene or 2,2-dioxo-1H-3-oxa-2-thia-1-aza-phenalene, provided that no more than one L—Q—$R^q$ group is present.

Heteroarylium refers to heteroaryl groups bearing a quaternary nitrogen atom and thus a positive charge. Examples include the following:

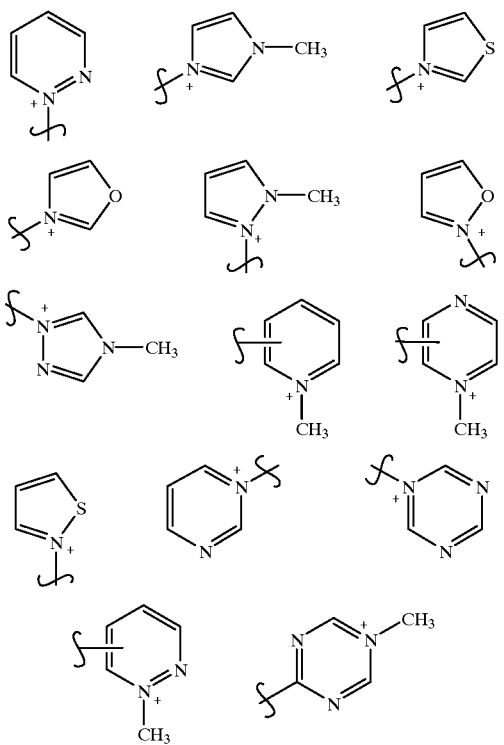

When a charge is shown on a particular nitrogen atom in a ring which contains one or more additional nitrogen atoms, it is understood that the charge may reside on a different nitrogen atom in the ring by virtue of charge resonance that occurs.

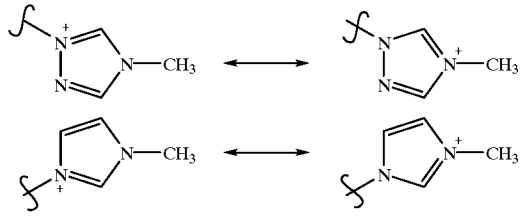

The imidazolium group:

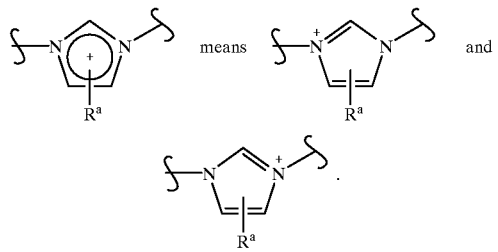

The term "heterocycloalkyl" refers to a cycloalkyl group (nonaromatic) in which one of the carbon atoms in the ring is replaced by a heteroatom selected from O, S or N, and in which up to three additional carbon atoms may be replaced by hetero atoms.

The terms "quaternary nitrogen" and "positive charge" refer to tetravalent, positively charged nitrogen atoms including, e.g., the positively charged nitrogen in a tetraalkylammonium group (e.g. tetramethylammonium), heteroarylium, (e.g., N-methylpyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

Halogen and "halo" refer to bromine, chlorine, fluorine and iodine.

When a group is termed "substituted", unless otherwise indicated, this means that the group contains from 1 to 4 substituents thereon.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification.

In some of the carbapenem compounds of the present invention, M is a readily removable carboxyl protecting group, and/or P represents a hydroxyl which is protected by a hydroxyl-protecting group. Such conventional protecting groups consist of groups which are used to protectively block the hydroxyl or carboxyl group during the synthesis procedures described herein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of carboxyl protecting groups include allyl, benzhydryl, 2-naphthylmethyl, benzyl, silyl such as t-butyldimethylsilyl (TBDMS), phenacyl, p-methoxybenzyl, o-nitrobenzyl, p-methoxyphenyl, p-nitrobenzyl, 4-pyridylmethyl and t-butyl.

Examples of suitable hydroxy protecting groups include triethylsilyl, t-butyldimethylsilyl, o-nitrobenzyloxycarbonyl, p-nitrobenzyloxycarbonyl, benzyloxycarbonyl, allyloxycarbonyl, t-butyloxycarbonyl, 2,2,2-trichloroethyloxycarbonyl and the like.

The carbapenem compounds of the present invention are useful per se and in their pharmaceutically acceptable salt and ester forms for the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, such as palatability, absorption, distribution, metabolism and excretion. Other factors, more practical in nature, which are also important in the selection, are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds.

With respect to —$CO_2M$, which is attached to the carbapenem nucleus at position 3, this represents a carboxylic acid group (M represents H), a carboxylate anion (M represents a negative charge), a pharmaceutically acceptable carboxylic acid salt (M represents a salt forming group), a pharmaceutically acceptable ester (M represents an ester forming group) or a carboxylic acid protected by a protecting group (M represents a carboxyl protecting group).

The pharmaceutically acceptable salts referred to above may take the form of a carboxylate —COOM, where M is a negative charge, which is balanced by a positively charged Q group. If the positively charged Q group contains more than one positive charge, a negatively charged counterion is present which in combination with the carboxylate anion, provides overall charge neutrality. Other pharmaceutically acceptable counterions may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above also include acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

Acid addition salts of the compounds of formula I include compounds that contain a protonated, basic moiety in R. Compounds containing a basic moiety in R are capable of protonation in aqueous media near pH 7, so that the basic moiety can exist as an equilibrium mixture of its neutral form and acid addition (protonated) form. The more basic the group, the greater the degree of protonation near pH 7. For example, —NR$^f$R$^g$ would likely be present in its protonated form (—N$^+$HR$^f$R$^g$Z$^-$) at the appropriate pH, where Z$^-$ is a charge balancing group. All such compounds are included in the present invention.

The pharmaceutically acceptable esters are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. These are also referred to as "biolabile esters".

Biolabile esters are biologically hydrolizable, and may be suitable for oral administration, due to good absorption through the stomach or intenstinal mucosa, resistance to gastric acid degradation and other factors. Examples of biolabile esters include compounds in which M represents an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. These groups can be substituted in the alkyl or aryl portions thereof with acyl or halo groups. The following M species are examples of biolabile ester forming moieties.: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

Y$^-$ can be present or absent as necessary to maintain the appropriate charge balance. When present, these represent pharmaceutically acceptable counterions. Most anions derived from inorganic or organic acids are suitable. Representative examples of such counterions are the following: acetate, adipate, aminosalicylate, anhydromethylenecitrate, ascorbate, aspartate, benzoate, benzenesulfonate, bromide, citrate, camphorate, camphorsulfonate, chloride, estolate, ethanesulfonate, fumarate, glucoheptanoate, gluconate, glutamate, lactobionate, malate, maleate, mandelate, methanesulfonate, pantothenate, pectinate, phosphate/diphosphate, polygalacturonate, propionate, salicylate, stearate, succinate, sulfate, tartrate and tosylate. Other suitable anionic species will be apparent to the ordinarily skilled chemist.

Likewise, when more than one negative charge is necessary to maintain charge neutrality, the counterion indicator may represent a specie with more than one negative charge, such as malonate, tartrate or ethylenediaminetetraacetate (EDTA), or two or more monovalent anions, such as chloride, etc. When a multivalent negatively charged counterion is present with a carbapenem which bears a net single positive charge, an appropriate number of carbapenem molecules can be found in association therewith to maintain the overall charge balance and neutrality.

Numbering and nomenclature used in naming the sultam side chains are as follows:

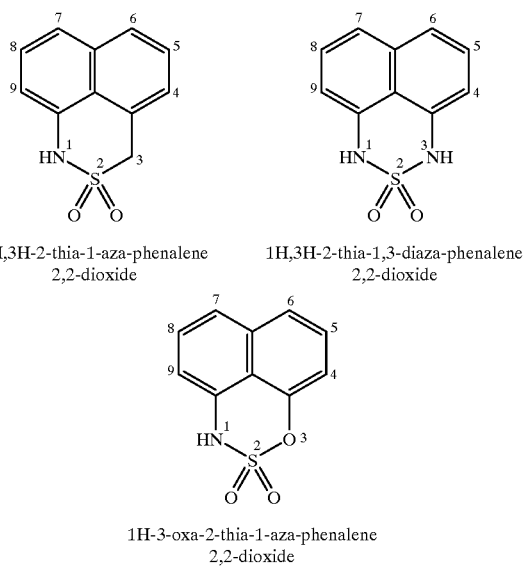

1H,3H-2-thia-1-aza-phenalene 2,2-dioxide 1H,3H-2-thia-1,3-diaza-phenalene 2,2-dioxide 1H-3-oxa-2-thia-1-aza-phenalene 2,2-dioxide When L is a $C_{1-4}$ straight or branched alkylene group that is interrupted or terminated by 1–2 of O, S, NR$^a$, C(O), CO$_2$ and C(O)NR$^a$, the interruptingterminating moiety or moieties can be at either end of the alkylene group, as well as interrupting the alkylene group when 2–4 carbon atoms are present. When 2 such groups are present, they may be separate or together. Hence, interrupting or terminating groups such as OC(O) and OCO$_2$ are included.

Similarly, when R$^a$ is $C_{1-6}$ alkyl, straight or branched, interrupted or terminated by 1–2 of O, S, NR$^a$, C(O), C(O)O, C(O)NR$^a$, —CH=CH—, —Het(R$^b$)$_3$—, —C(O)Het(R$^b$)$_3$—, —C(O)NR$^a$Het(R$^b$)$_3$—,

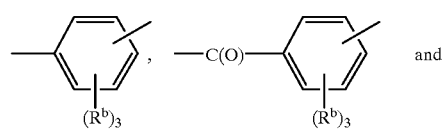

-continued

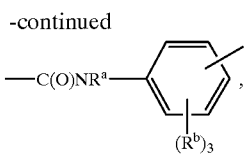

said $R^q$ being unsubstituted or substituted with 1–3 $R^c$ groups, the interrupting/terminating groups may be separate or together, and may be at the end or ends of the alkyl group, and further may be between the alkyl group and a substituent $R^c$.

When an $R^q$ is substituted with at least 2 $R^c$ groups, these may be taken in combination with any intervening atoms to represent a 3–6 membered carbocyclic ring, said ring being optionally interrupted by 1–3 of O, S, $NR^g$ and C(O), and unsubstituted or substituted with 1–3 $R^e$ groups. Examples of groups which are represented by two $R^c$ groups in combination include the following:

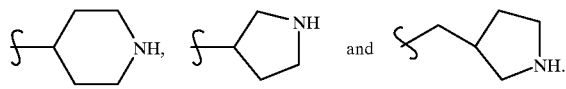

A subset of compounds of formula I which is of interest relates to those compounds where $R^1$ represents methyl. Within this subset, all other variables are as originally defined.

Another subset of compounds of formula I which is of interest relates to those compounds where $CO_2M$ represents a carboxylate anion. Hence, M in this instance represents a negative charge which is balanced by a positively charged group, such as in the positively charged Q group. Likewise, if the positively charged Q group contains more than one positive charge, a negatively charged counterion may be present which in combination with the carboxylate anion, provides overall charge neutrality.

Another subset of compounds of formula I that is of interest relates to those compounds where P represents hydroxyl or hydroxyl protected by a hydroxyl protecting group. Within this subset, all other variables are as originally defined.

Another subset of compounds of formula I that is of interest relates to compounds where one R represents L—Q—Rq and all other R groups represent H, halo or $C_{1-4}$ alkyl unsubstituted or substituted with 1–3 groups selected from $R^e$. Within this subset, all other variables are as originally defined. An embodiment of this subset is realized when L represents —$CH_2$— or —$CH_2CH_2$—. Another embodiment of this subset is realized when Q represents

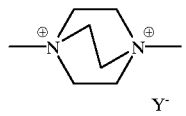

wherein $Y^-$ represents a charge balancing group. Within this subset, all other variables are as originally defined. Still another embodiment of this subset is realized when $R^q$ is straight or branched $C_{1-6}$ alkyl, substituted with 1–3 $R^c$ groups. Within this subset, all other variables are as originally defined.

Another subset of compounds of formula I that is of interest relates to compounds where X is $CR^2R^3$. Within this subset, all other variables are as originally defined.

Another subset of compounds of formula I that is of interest relates to compounds where X is $NR^2$. Within this subset, all other variables are as originally defined.

Another subset of compounds of formula I that is of interest relates to compounds where X is O. Within this subset, all other variables are as originally defined.

Another subset of compounds of formula I that is of interest relates to compounds where R is H, halo or $C_{1-4}$ alkyl unsubstituted or substituted with 1–3 groups selected from $R^e$. Within this subset, all other variables are as originally defined.

A preferred subset of compounds of formula I which is of interest relates to those compounds wherein:

$R^1$ represents $CH_3$;

$CO_2M$ represents a carboxylate anion;

P represents hydroxyl or hydroxyl protected by a hydroxyl protecting group; and one R is L—Q—$R^q$ and each remaining R is independently H, halo or $C_{1-4}$ alkyl unsubstituted or substituted with 1–3 groups selected from $R^e$; all other variables are as originally described.

In one embodiment of this invention $R^a$ is H or $C_{1-6}$ alkyl;

$R^d$ is H or $C_{1-4}$ alkyl, or $R^a$ and $R^d$ taken together with any intervening atoms represent a 4–6 membered ring;

$R^e$ is halo, $OR^a$, $NR^aR^d$ or $CONR^aR^d$;

L represents —$CH_2$— or —$CH_2CH_2$—;

Q represents

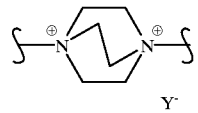

wherein $Y^-$ represents a charge balancing group and $R^q$ is straight or branched $C_{1-6}$ alkyl, optionally interrupted by $C(O)NR^a$ or

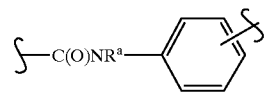

and substituted with 1–3 $R^c$ groups, and $R^c$ is as originally defined.

Representative examples of compounds of the invention are found in Table I.

TABLE I

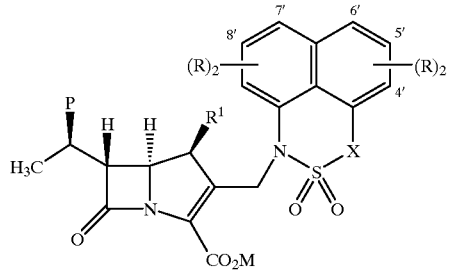

P = H, OH, or F and $R^1$ =H, or Methyl

| | X | Substituent(s) R | M |
|---|---|---|---|
| 1 | $NCH_3$ | H | Na |
| 2 | $CH_2$ | H | Na |

TABLE I-continued

[Structure: carbapenem core with P-substituted ethyl group, R¹ substituent, and CH₂-N-SO₂-X linker to naphthalene ring system bearing (R)₂ substituents at positions 4', 5', 6', 7', 8'; CO₂M group]

P = H, OH, or F and R¹ = H, or Methyl

| # | X | Substituent(s) R | M |
|---|---|---|---|
| 3 | O | H | Na |
| 4 | NCH₃ | 5'-(CH₂)ₙ-N⁺(imidazole)-N-CH₃, n = 1,2 | ⊖ |
| 5 | NCH₃ | 6'-(CH₂)ₙ-N⁺(imidazole)-N-CH₃, n = 1,2 | ⊖ |
| 6 | CH₂ | 6'-(CH₂)ₙ-N⁺(imidazole)-N-CH₃, n = 1,2 | ⊖ |
| 7 | NCH₃ | 6'-(CH₂)ₙ-N⁺(imidazole)-N-CH₂CH₂OH, n = 1,2 | ⊖ |
| 8 | NCH₃ | 4'-(CH₂)ₙ-N⁺(DABCO)-N⁺-CH₂CONH₂, Cl⊖, n = 1,2 | ⊖ |
| 9 | NCH₃ | 5'-(CH₂)ₙ-N⁺(DABCO)-N⁺-CH₂CONH₂, Cl⊖, n = 1,2 | ⊖ |
| 10 | NCH₃ | 6'-(CH₂)ₙ-N⁺(DABCO)-N⁺-CH₂CONH₂, Cl⊖, n = 1,2 | ⊖ |
| 11 | CH₂ | 4'-(CH₂)ₙ-N⁺(DABCO)-N⁺-CH₂CONH₂, Cl⊖, n = 1,2 | ⊖ |
| 12 | CH₂ | 5'-(CH₂)ₙ-N⁺(DABCO)-N⁺-CH₂CONH₂, Cl⊖, n = 1,2 | ⊖ |
| 13 | CH₂ | 6'-(CH₂)ₙ-N⁺(DABCO)-N⁺-CH₂CONH₂, Cl⊖, n = 1,2 | ⊖ |
| 14 | O | 6'-(CH₂)ₙ-N⁺(DABCO)-N⁺-CH₂CONH₂, Cl⊖, n = 1,2 | ⊖ |
| 15 | NCH₂CH₃ | 6'-(CH₂)ₙ-N⁺(DABCO)-N⁺-CH₂CONH₂, Cl⊖, n = 1,2 | ⊖ |
| 16 | CHCH₃ | 6'-(CH₂)ₙ-N⁺(DABCO)-N⁺-CH₂CONH₂, Cl⊖, n = 1,2 | ⊖ |
| 17 | C(CH₃)₂ | 6'-(CH₂)ₙ-N⁺(DABCO)-N⁺-CH₂CONH₂, Cl⊖, n = 1,2 | ⊖ |
| 18 | NCH₃ | 5'-(CH₂)ₙ-N⁺(DABCO)-N⁺-(CH₂)₃OH, Cl⊖, n = 1,2 | ⊖ |
| 19 | NCH₃ | 6'-(CH₂)ₙ-N⁺(DABCO)-N⁺-(CH₂)₃OH, Cl⊖, n = 1,2 | ⊖ |

TABLE I-continued

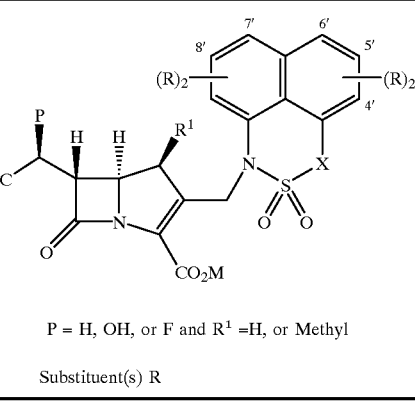

P = H, OH, or F and R¹ =H, or Methyl

| X | Substituent(s) R | | M |
|---|---|---|---|
| 20 CH₂ | 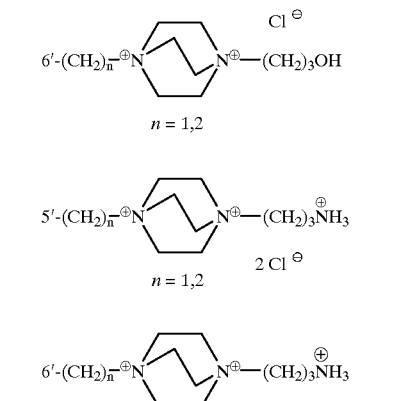 | Cl⁻ | ⊖ |
| 21 NCH₃ | 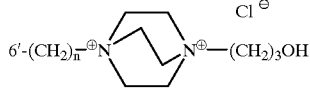 | 2 Cl⁻ | ⊖ |
| 22 NCH₃ | 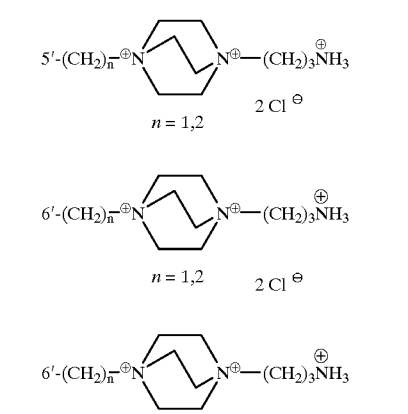 | 2 Cl⁻ | ⊖ |
| 23 CH₂ | 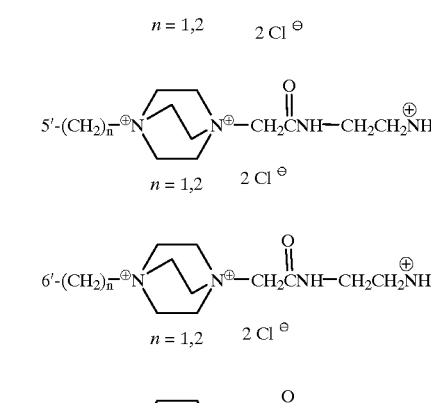 | 2 Cl⁻ | ⊖ |
| 24 NCH₃ | 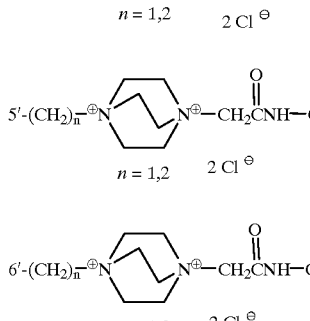 | 2 Cl⁻ | ⊖ |
| 25 NCH₃ | 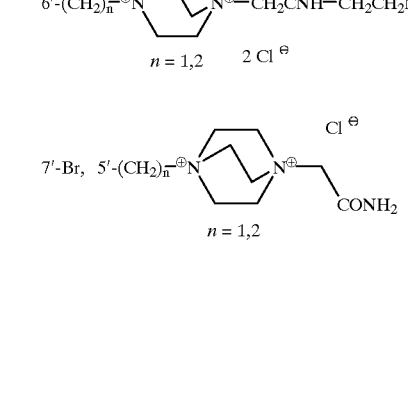 | 2 Cl⁻ | ⊖ |
| 26 CH₂ |  | 2 Cl⁻ | ⊖ |
| 27 NCH₃ | 7'-Br, 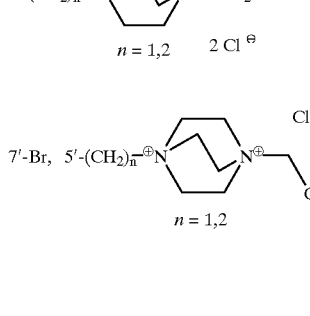 | Cl⁻ | ⊖ |

TABLE I-continued

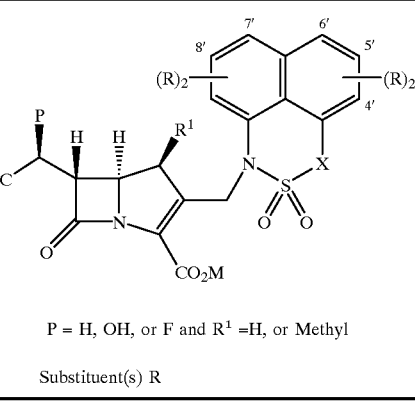

P = H, OH, or F and R¹ =H, or Methyl

| X | Substituent(s) R | | M |
|---|---|---|---|
| 28 NCH₃ | 7'-Cl, 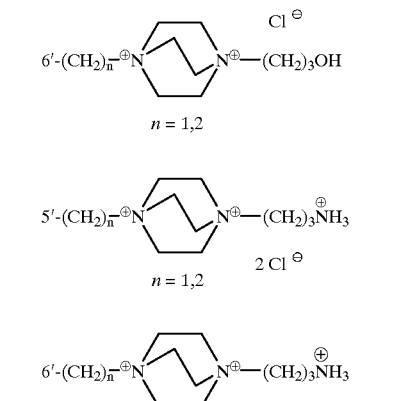 | Cl⁻ | ⊖ |
| 29 NCH₃ | 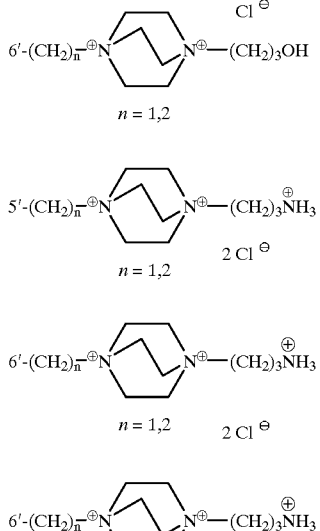 | | ⊖ |
| 30 NCH₃ | 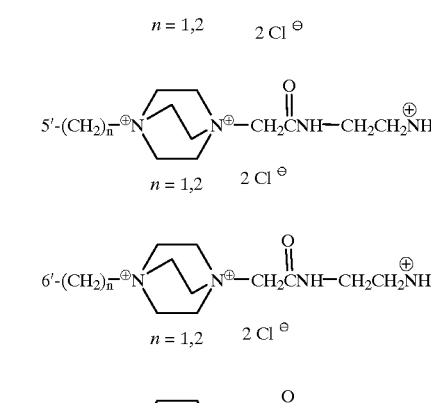 | | ⊖ |
| 31 NCH₃ | 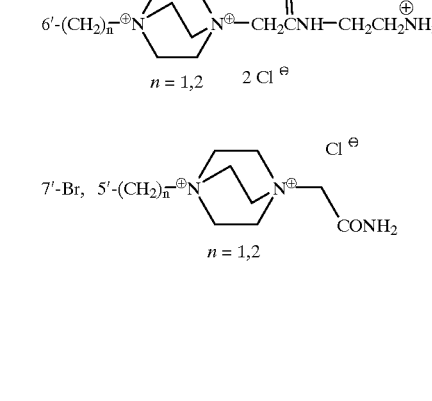 | Cl⁻ | ⊖ |
| 32 NCH₃ | 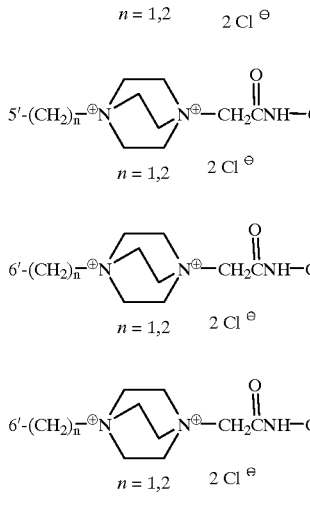 | 2 Cl⁻ | ⊖ |
| 33 NCH₃ | 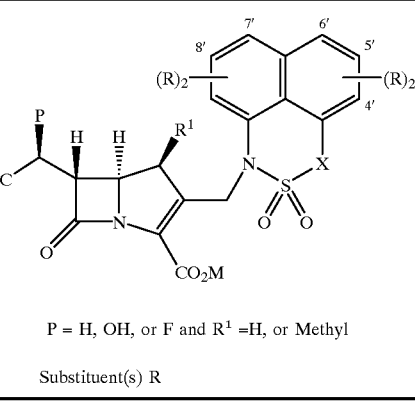 | 2 Cl⁻ | ⊖ |
| 34 CH₂ | 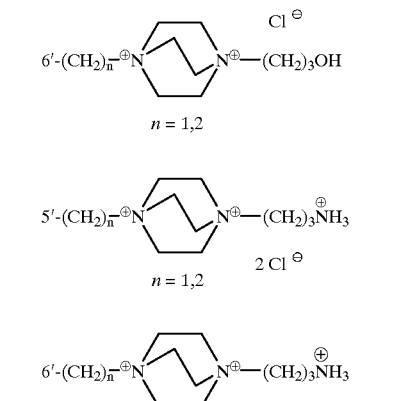 | | ⊖ |
| 35 NCH₃ | 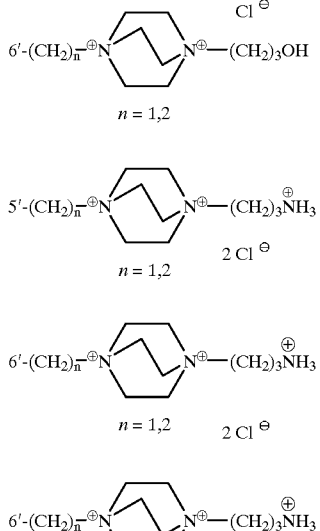 | | ⊖ |

The compounds of the present invention are prepared by reacting a suitably protected, activated 2-hyroxymethyl-carbapen-2-em-3-carboxylate with a 1H,3H-2-thia-1-aza-phenalene 2,2-dioxide, 1H,3H-2-thia-1,3-diaza-phenalene 2,2-dioxide or 1H-3-oxa-2-thia-1-aza-phenalene 2,2-dioxide group, modifying the thus-introduced side chain as desired, and then removing any protecting groups which are present to afford the desired final product. The process is illustrated using the general conditions shown in the accompanying flow charts.

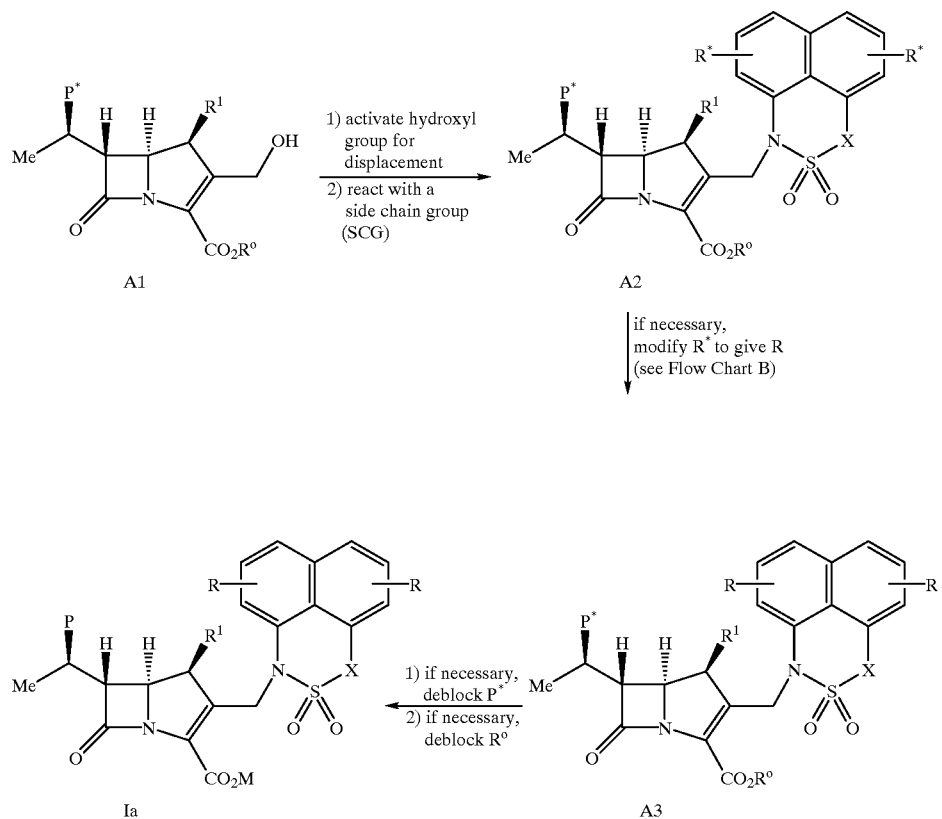

Flow Chart A

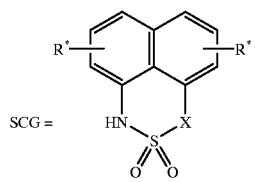

SCG =

P* = H, F, or a protected hydroxy group
R° = carboxyl protecting group or a pharmaceutically acceptable ester group
R* = R or a precursor to R
P, R¹, M, R, and X are as previously defined Flow Chart B

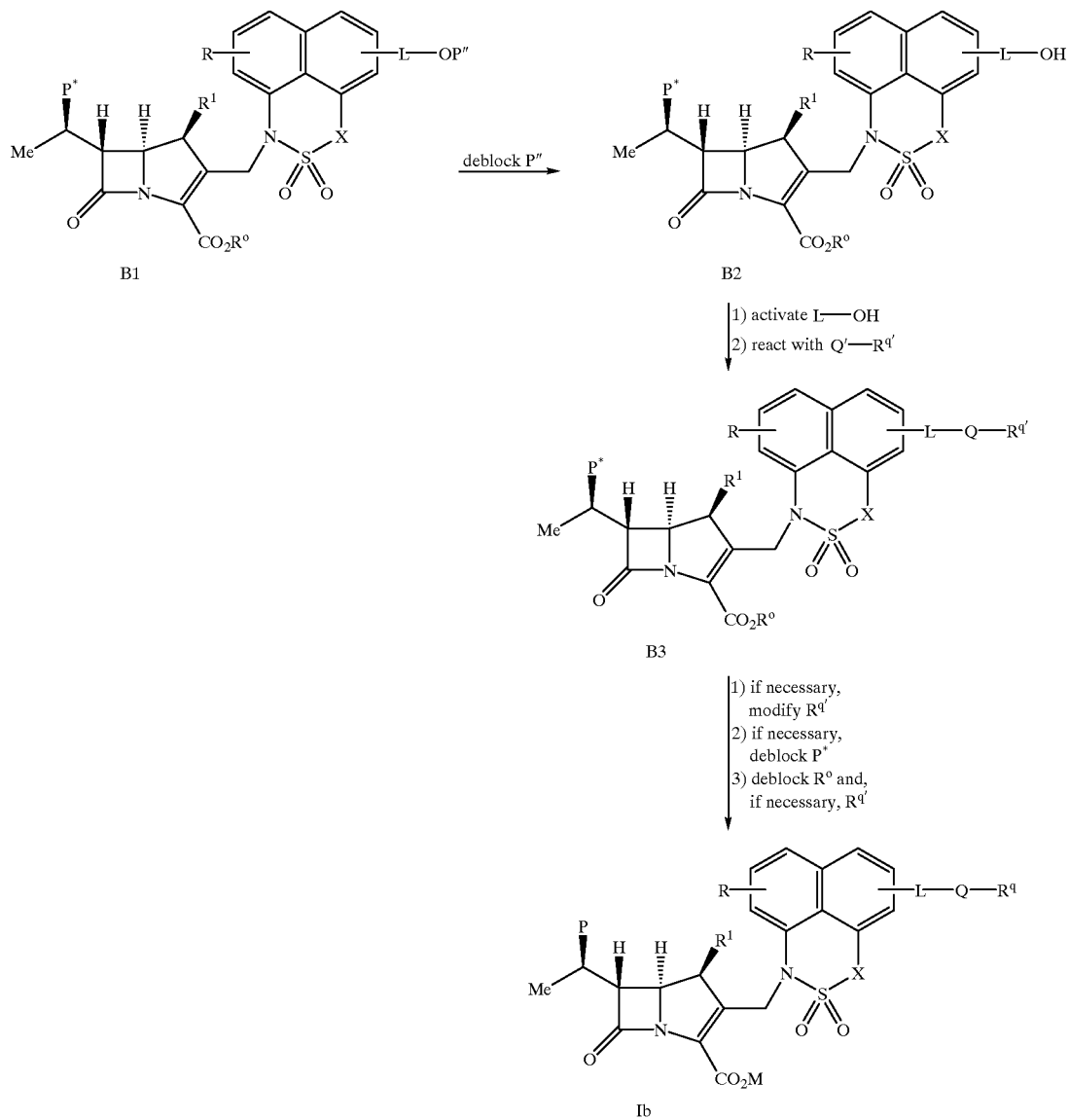

P″ = hydroxyl protecting group
P* = H, F, or a protected hydroxy group
R° = carboxyl protecting group or a pharmaceutically acceptable ester group
Q′ = neutral or cationic precursor to Q
$R^{q'}$ = $R^q$ or a modified/protected precursor to $R^q$
P, $R^1$, M, R, L, Q, $R^q$, and X are as previously defined With reference to Flow Charts A and B above, P, $R^1$, R, M, X, L, Q and $R^q$ are as defined with respect to the compounds of formula I.

P* represents H, F or a protected hydroxyl group.

R° represents a carboxyl protecting group.

R* represents a group selected from R or a group that is modified as necessary in the course of the synthesis of a compound of formula I to afford a member of R, thus R* can be viewed as R or a precursor to R.

P″ represents a hydroxyl protecting group.

Q′—$R^{q'}$ represents a neutral or monocationic group that reacts with the intermediate B2 (upon activation of B2) in a manner which results in the incorporation in the final product of the member of the group defined as Q—$R^q$ above, thus Q′—$R^{q'}$ may be viewed as a precursor for Q—$R^q$.

$R^{q'}$ represents a group selected from $R^q$ or a group that is modified or deprotected as necessary in the course of the synthesis of a compound of formula I so as to afford a member of $R^q$, thus $R^{q'}$ can be viewed as $R^q$ or as a precursor to $R^q$.

The 1H,3H-2-thia-1-aza-phenalene 2,2-dioxide, 1H,3H-2-thia-1,3-diaza-phenalene 2,2-dioxide or 1H-3-oxa-2-thia-1-aza-phenalene 2,2-dioxide side chain group (SCG) used in the synthesis of the compounds of the present invention have, in some cases, been described in the chemical literature. In other cases, precursor compounds which may be readily converted to the requisite SCG have been described in the literature. In cases where the requisite SCG is not known in the literature it is necessary to synthesize the SCG by a newly developed synthesis. One skilled in the art can adapt a previously published synthesis of an analogous SCG to prepare the requisite compound in a straightforward manner without undue experimentation.

The 1H,3H-2-thia-1-aza-phenalene 2,2-dioxide, 1H,3H-2-thia-1,3-diaza-phenalene 2,2-dioxide or 1H-3-oxa-2-thia-1-aza-phenalene 2,2-dioxide side chain group (SCG) is initially reacted with a suitably protected carbapen-2-em-3-carboxylate having an activated hydroxymethyl group at the 2-position.

The carbapenem nucleus having a —$CH_2OH$ substituent at position 2 can be obtained in accordance with Schmitt, S. M. et al., *J. Antibiotics* 41(6): 780–787 (1988), the teachings of which are incorporated herein by reference.

The carboxylic acid group at C-3 of the carbapenem is generally protected as a carboxyl protecting group such as p-nitrobenzyl (PNB), allyl, p-methoxybenzyl, trichloroethyl, 2-trimethylsilylethyl, and the like. Furthermore, the hydroxyl group of the 6-(hydroxyethyl) side-chain is optionally protected with a hydroxyl protecting group such as trimethylsilyl (TMS), triethylsilyl (TES), tert-butyldimethylsilyl (TBDMS), tert-butyldiphenylsilyl (TBDPS), acetyl, allyloxycarbonyl, 2-trimethylsilylethoxy carbonyl, 2-trichloroethoxycarbonyl and the like.

The addtion of 1H,3H-2-thia-1-aza-phenalene 2,2-dioxide, 1H,3H-2-thia-1,3-diaza-phenalene 2,2-dioxide or 1H-3-oxa-2-thia-1-aza-phenalene 2,2-dioxide side chain group (SCG) to the carbapenem is accomplished by treating a solution of the hydroxymethyl-carbapenem and the 1H,3H-2-thia-1-aza-phenalene 2,2-dioxide, 1H,3H-2-thia-1,3-diaza-phenalene 2,2-dioxide or 1H-3-oxa-2-thia-1-aza-phenalene 2,2-dioxide group side chain group in a suitable solvent such as tetrahydrofuran (THF), diethyl ether, acetonitrile, dimethylformamide (DMF), benzene, dichloromethane, chloroform, and the like with a (premixed) suitable activating reagent such as diethyl azodicarboxylate (DEAD)/triphenylphosphine, diisopropyl azodicarboxylate (DIAD)/tributylphosphine, and the like, at a temperature between about –20° C. and 35° C. for about 5 to 90 minutes.

Alternatively, the 1H,3H-2-thia-1-aza-phenalene 2,2-dioxide, 1H,3H-2-thia-1,3-diaza-phenalene 2,2-dioxide or 1H-3-oxa-2-thia-1-aza-phenalene 2,2-dioxide and carbapenem can be mixed together with either the azodicarboxylate or the phosphine reagent in a suitable solvent and the other component of the activating reagent (the phosphine or the azodicarboxylate, respectively) can be added to that mixture. Once the sultam side chain group carbapenem and activating reagent(s) have been mixed, the reaction is allowed to proceed at a temperature between about –20° C. and 35° C. for about 5 to 90 minutes.

The resulting mixture is then subjected to a standard work-up procedure familiar to those skilled in the art to afford a crude 2-(2,2-dioxo-1H,3H-2-thia-1-aza-phenalenyl, 2,2-dioxo-1H,3H-2-thia-1,3-diaza-phenalenyl or 2,2-dioxo-1H-3-oxa-2-thia-1-aza-phenalenyl) methyl substituted carbapenem which is purified, if necessary, by recrystallization or by chromatography on silica gel, eluting with a suitable solvent or mixture of two or more solvents, such as hexane, ethyl acetate, ether, benzene, dichloromethane, chloroform, acetone, methanol and the like.

In some cases, it is necessary to modify substituent R* in intermediate A2 to produce the desired substituent R in final product I. Modification of the R* substituent is generally best accomplished before the removal of the protecting groups P* and $R^o$. This process is illustrated in Flow Chart B in which intermediate B1 is an example of intermediate A2 wherein one of the R* groups is a precursor to the substituent L—Q—$R^q$. The skilled artisan should note that the substituent L—Q—$R^q$ can be located in either of the phenyl rings of the final product Ib even though the scheme illustrates the process for one ring only.

In intermediate B1 of Flow Chart B, the substituent R* is represented as L—OP", wherein L is as previously defined and P" is a hydroxyl protecting group. Suitable protecting groups P" are trimethylsilyl and triethylsilyl. The trialkylsilyl group is easily removed by treatment with a strong acid such as trifluoromethane sulfonic acid, sulfuric acid, hydrochloric acid, or the the like in a solvent consisting of water plus a miscible organic solvent such as tetrahydrofuran, acetonitrile, or isopropanol. A positively charged substituent may be introduced into the side chain by first activating the hydroxyl group of L—OH by converting it to a suitable leaving group such as a triflate, mesylate, tosylate, iodide, chloride, bromide, and the like, and then displacing the resulting leaving group with a compound Q'—$R^{q'}$, such as N-methyl-imidazole, N-(2-hydroxyethyl)-imidazole, 1-methyl-4-aza-1-azoniabicyclo[2.2.2]octane, 1-(carbamoylmethyl)-4-aza-1-azoniabicyclo-[2.2.2.]-octane, 1-(3-hydroxyprop-1-yl)-4-aza-1-azoniabicyclo-[2.2.2.]-octane, and the like which contains a nitrogen atom that can act as a nucleophile.

In some cases, activation of the hydroxyl group and displacement by Q'—$R^{q'}$ to produce B3 may be accomplished in a single step by taking advantage of the basic character of compound Q'—$R^{q'}$ and using it as a base in the activation reaction.

The conversion of the hydroxyl group to a suitable leaving group is accomplished by treating the hydroxyl substituted compound in a suitable solvent such as dichloromethane, tetrahydrofuran, ether, benzene, and the like with an activating reagent, such as trifluoromethanesulfonic anhydride, methanesulfonic anhydride, toluenesulfonic anhydride, methanesulfonyl chloride, benzenesulfonyl chloride, toluenesulfonyl chloride, and the like in the presence of a suitable base such as triethylamine, tributylamine, diisopropylethylamine, and the like at a temperature between about –100° C. and 0° C. for about 5 to 120 minutes. The intermediate thus obtained contains a leaving group, which may be converted to an alternative leaving group, iodide, by treating a solution of the intermediate in a suitable solvent such as acetone, methyl ethyl ketone, and the like at about –10° C. to 50° C. with an excess of sodium iodide or potassium iodide for about 0.25 to 24 hours.

In many cases, the iodide is obtained in sufficiently pure form that it may be used without further purification. For ease of handling, the iodide, if not crystalline, may be lyophilized from benzene to afford an amorphous, easily handled, solid.

The activated hydroxyl group or iodide is displaced by reacting the activated intermediate with reagent Q'—$R^{q'}$. In some cases, activation and displacement of the hydroxyl group may be accomplished in a single step. The activating reagent is added to a solution of the hydroxyl substituted compound in the presence of a suitable base in a suitable solvent such as dichloromethane, tetrahydrofuran, ether, DMF, benzene, acetonitrile, DMSO, and the like as described in the preceding paragraphs. The resulting activated intermediate is treated with 1–3 molar equivalents of compound Q'—$R^{q'}$ at a temperature between about –78° C. and 50° C. for about 15 to 120 minutes. In some cases, it is desirable to form the activated intermediate in one solvent, isolate the activated intermediate, and conduct the displacement reaction in a different solvent. In other cases, the displacement may be conducted without isolation of the intermediate and, in cases where Q'—$R^{q'}$ is also used as a base, may even be concurrent with the formation of the activated intermediate.

In cases where the displacement reaction is best accomplished by using the iodide, a solution of the iodide is combined with an approximately equivalent amount (0.9–1.05 molar equivalents) of compound Q'—$R^{q'}$. A silver salt of a non-nucleophilic acid, such as silver trifluoromethanesulfonate, silver tetrafluoroborate and the like is then added. Although the reaction will proceed in the absence of the silver salt, the reaction proceeds more rapidly in the presence of the silver salt. In addition, the silver salt assists in the removal of the displaced iodide from the reaction mixture which can improve the efficiency of subsequent steps. The resulting mixture is then subjected to a standard work-up procedure familiar to those skilled in the art to afford a crude product which is purified, if necessary, by recrystallization or chromatography.

An alternative method for introducing a positive charge into the side chain may be applied to side chains (i.e. $R^*$ groups) that contain a nitrogen atom which may be quaternized by reaction with a suitable alkylating reagent AR, such as methyl iodide, methyl bromide, benzyl trichloroacetimidate, methyl trifluoromethanesulfonate, triethyloxonium tetrafluoroborate, and the like. Quaternization of the nitrogen atom in the side chain is effected by treating a solution of the compound with a slight excess (1.05 to 1.2 molar equivalents) of the alkylating reagent.

Modification of the substituent $R^q$, if necessary, and removal of the remaining protecting group(s) affords the final product (Ib). These transformations can be accomplished by a number of well known techniques depending on the protecting groups employed or the modifications required to transform $R^{q'}$ to $R^q$ or the protecting groups employed.

For example, when $R^q$ of the final product contains a primary amino group (—$NH_2$ or —$N^+H_3$ in its protonated form), the amino group would normally be present in $R^{q'}$ as a protected form or as a precursor group. Suitably protected forms of the amino group are allyloxycarbonylamino or p-nitrobenzyloxycarbonylamino whereas as suitable amine precursor is an azido group. The amino group is liberated by established methodology either concurrrent with or after the deblocking of P* and $R^o$. For example, the azido and p-nitrobenzyloxycarbonylamino groups can be converted to the amino group by catalytic hydrogenation and the allyloxycarbonylamino group provides the amino substituent on treatment with a palladium catalyst in the presence of an allyl scavenger.

The synthesis of the target compound is completed by removing any protecting groups which are present in the penultimate intermediate using standard techniques which are well known to those skilled in the art. The deprotected final product is then purified, as necessary, using standard techniques such as ion exchange chromatography, HPLC on reverse phase silica gel, MPLC on reverse phase polystyrene gel, and the like or by recrystallization.

The final product may be characterized structurally by standard techniques such as NMR, IR, MS, and UV. For ease of handling, the final product, if not crystalline, may be lyophilized from water to afford an amorphous, easily handled solid.

The compounds of the present invention are valuable antibacterial agents active against various Gram-positive and to a lesser extent Gram-negative bacteria, and accordingly find utility in human and veterinary medicine.

Many of compounds of the present invention are biologically active against MRSA/MRCNS. In vitro antibacterial activity is predictive of in vivo activity when the compounds are administered to a mammal infected with a susceptible bacterial organism.

Using standard susceptibility tests, the compounds of the invention are determined to be active against MRSA.

The compounds of the invention can be formulated in pharmaceutical compositions by combining the compound with a pharmaceutically acceptable carrier. Examples of such carriers are set forth below.

The compounds may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral composions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ dosage amounts in the range of from about 250 mg to 1000 mg. In parenteral administration, the unit dosage will typically include the pure compound in sterile water solution or in the form of a soluble powder intended for solution, which can be adjusted to neutral pH and isotonic.

The invention described herein also includes a method of treating a bacterial infection in a mammal in need of such treatment comprising administering to said mammal a compound of formula I in an amount effective to treat said infection.

The preferred methods of administration of the Formula I antibacterial compounds include oral and parenteral, e.g., i.v. infusion, i.v. bolus and i.m. injection.

For adults, about 5–50 mg of Formula I antibacterial compound per kg of body weight given one to four times daily is preferred. The preferred dosage is 250 mg to 1000 mg of the antibacterial given one to four times per day. More specifically, for mild infections a dose of about 250 mg two or three times daily is recommended. For moderate infections against highly susceptible gram positive organisms a dose of about 500 mg three or four times daily is recommended. For severe, life-threatening infections against organisms at the upper limits of sensitivity to the antibiotic, a dose of about 1000–2000 mg three to four times daily may be recommended.

For children, a dose of about 5–25 mg/kg of body weight given 2, 3, or 4 times per day is preferred; a dose of 10 mg/kg is typically recommended.

The compounds of Formula I are of the broad class known as carbapenems. Many carbapenems are susceptible to attack by a renal enzyme known as dehydropeptidase (DHP). This attack or degradation may reduce the efficacy of the carbapenem antibacterial agent. Many of the compounds of the present invention, on the other hand, are less subject to such attack, and therefore may not require the use of a DHP inhibitor. However, such use is optional and contemplated to be part of the present invention. Inhibitors of DHP and their use with carbapenems are disclosed in, e.g., [European Patent Application Nos. 79102616.4, filed Jul. 24, 1979 (Patent No. 0 007 614); and 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. The cited European Patent Applications define the procedure for determining DHP susceptibility of the present carbapenems and disclose suitable inhibitors, combination compositions and methods of treatment. A preferred weight ratio of Formula I compound: DHP inhibitor in the combination compositions is about 1:1.

A preferred DHP inhibitor is 7-(L-2-amino-2-carboxyethylthio)-2-(2,2-dimethylcyclopropanecarboxamide)-2-heptenoic acid or a useful salt thereof.

The invention is further described in connection with the following non-limiting examples.

PREPARATIVE EXAMPLE 1

2,2-Dioxo-1-methyl-1H,3H-2-thia-1,3-diaza-phenalene

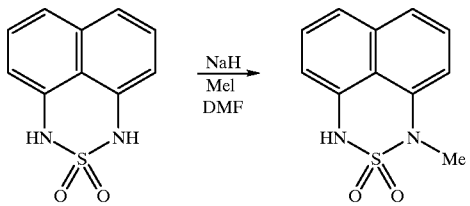

2,2-Dioxo-1H,3H-2-thia-1,3-diaza-phenalene (220 mg, 1 mmol) was added to an ice-cold slurry of sodium hydride (41 mg of a 61.1% dispersion in mineral oil, 1.04 mmol) in anhydrous dimethyl formamide (2 mL). The mixture was stirred at 0–5° C. and under a nitrogen atmosphere for 20 minutes, then treated with methyl iodide (0.068 mL, 1.09 mmol). After stirring an additional 30 minutes at 0–5° C., the mixture was diluted with ethyl ether (40 mL) and extracted with water (20 mL, 2×10 mL). The combined aqueous extracts were acidified to pH 1 with conc. hydrochloric acid and extracted with diethyl ether (20 mL, 2×10 mL). The organic extracts were washed with brine (20 mL), dried over sodium sulfate, filtered, and evaporated under vacuum to a solid residue (216 mg). Proton NMR showed a 29:27:44 mixture of starting material:monomethyl product:dimethyl product. The product mixture was purified by preparative layer chromatography on two 1 mm×20 cm×20 cm silica gel GF plates. The plates were developed with 10% ethyl acetate in dichloromethane. The band at $R_f$ 0.47–0.67 was removed and eluted with ethyl acetate. Evaporation of the solvent under vacuum gave the title comound (44 mg) as a solid.

$^1$H NMR (DMSO-$d_6$, 500 Mhz) δ 3.22 (s, $CH_3$), 6.94 (d, aryl-H), 7.10 (d, aryl-H), 7.46 (t, aryl-H), 7.50 (t, aryl-H), and 7.61 (m, two aryl-H).

The starting material for the synthesis of the title compound was prepared from 1,8-diamino-naphthalene (known in the art) according to the procedure described in Forster, D. L., Gilchrist, T. L., and Rees, C. W. *J. Chem. Soc. C* 1971, 993.

EXAMPLE 1

Sodium (1S,5R,6S)-6-[1(R)-hydroxy-ethyl]-1-methyl-2-(3-methyl-2,2-dioxy-2,3-dihydro-2-thia-1,3-diaza-phenylene-1-ylmethyl)-carbapen-2-EM-3-carboxylate

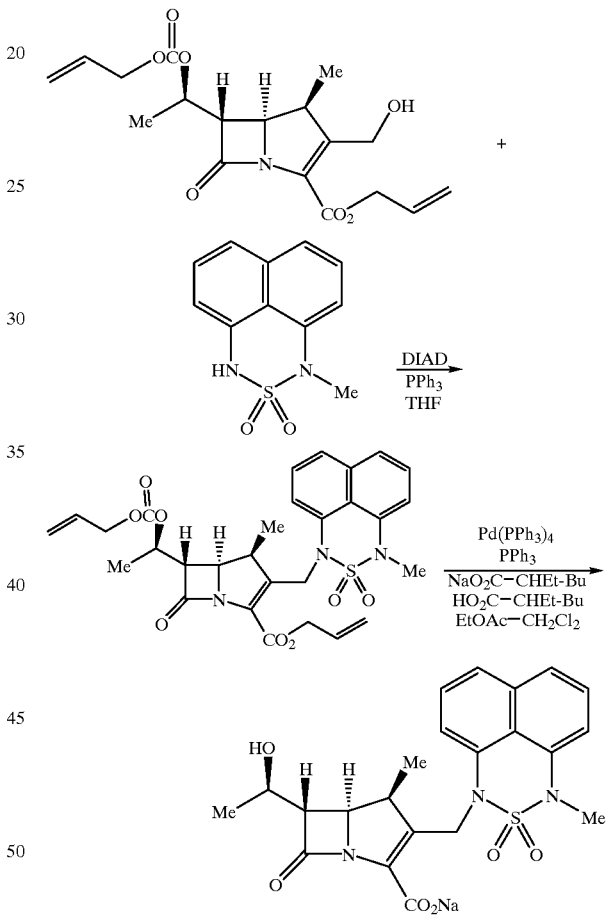

Step 1: Allyl (1S,5R,6S)-6-[1(R)-allyloxycarbonyloxy-ethyl]-1-methyl-2-(3-methyl-2,2-dioxo-2,3-dihydro-2-thia-1,3-diaza-phenylen-1-ylmethyl)-carbapen-2-em-3-carboxylate A solution of allyl (1S,5R,6S)-6-[1(R)-allyloxycarbonyloxy-ethyl]-2-hydroxymethyl-1-methyl-carbapen-2-em-3-carboxylate (38.3 mg, 0.105 mmol), 3-methyl-2,2-dioxo-2,3-dihydro-2-thia-1,3-diaza-phenylene (27.0 mg, 0.115 mmol), and triphenylphosphine (33.0 mg, 0.126 mmol) in anhydrous tetrahydrofuran (0.77 mL) was cooled in an ice bath and stirred under a nitrogen atmosphere. Diisopropyl azodicarboxylate (0.0248 mL, 0.126 mmol) was added dropwise by syringe. The mixture was stirred at 5° C. for 30 minutes, then diluted with chloroform (20 mL) and washed with 5% aqueous sodium bicarbonate (2×10 mL) and brine (10 mL). The solution was dried over sodium sulfate, filtered, and evaporated under vacuum to a gum (124 mg). The gum was purified by prreparative layer chromatography on a 1 mm×20 cm×20 cm silica gel GF plates. The plate was developed with 2% ethyl acetate in dichloromethane. The product band ($R_f$ 0.32–0.49) was removed and eluted with ethyl acetate to afford allyl (1S,5R,6S)-6-[1(R)-allyloxycarbonyloxy-ethyl]-1-methyl-2-(3-methyl-2,2-dioxo-2,3-dihydro-2-thia-1,3-diaza-phenylen-1-ylmethyl)-carbapen-2-em-3-carboxylate (39 mg) as an oil.

Step 2: Sodium (1S,5R,6S)-6-[1(R)-hydroxy-ethyl]-1-methyl-2-(3-methyl-2,2-dioxo-2,3-dihydro-2-thia-1,3-diaza-phenylen-1-ylmethyl)-carbapen-2-em-3-carboxylate The product from step 1 (39 mg, 0.067 mmol) and triphenylphosphine (5.3 mg, 0.020 mmol) were dissolved in 1:1 ethyl acetate-dichloromethane (1.3 mL). The solution was cooled in an ice bath and treated successively with 0.5M sodium 2-ethyl-hexanoate in ethyl acetate (0.148 mL, 0.074 mmol), 2-ethyl-hexanoic acid (0.0118 mL, 0.074 mmol), and tetrakis(triphenylphosphine)palladium(0) (7.7 mg, 0.0067 mmol). The mixture was stirred at 0–5° C. for 30 minutes to give a clear, amber solution. The solution was diluted with diethyl ether (6.5 mL) to provide an off-white precipitate. The solid was collected by centrifugation, washed with ether (2×5 mL), and dried under vacuum. The solid was dissolved in water (1 mL) containing a few drops of acetonitrile and streaked onto a 1 mm×20 cm×20 cm RPS-F plate which was developed with 4:1 water-acetonitrile in an ice cooled tank. The UV visible band at $R_f$ 0.20–0.38 was removed and eluted with 4:1 acetonitrile—water (4×10 mL). The eluent was diluted with water (10 mL), washed with hexanes (2×20 mL), concentrated under vacuum to 5.6 mL volume, filtered through a 0.45 micron CR acrodisc, and lyophilized to provide the title compound (19.9 mg) as a white, amorphous solid.

$^1$H NMR (77:23 $D_2O$-$CD_3CN$, 500 Mhz) δ 1.30 (d, 1—$CH_3$), 1.35 (d, $CH_3CHOH$), 3.23 (m, H-1), 3.48 (dd, H-6), 3.56 (s, $NCH_3$), 4.09 (dd, H-5), 4.30 (m, $CH_3CHOH$), 4.86 and 5.45 (two d's, 2-$CH_2$), 7.39 (m, two aryl-H), 7.72 (t, aryl-H), 7.76 (t, aryl-H), and 7.92 (m, two aryl-H);

UV (0.1M pH 7.0 MOPS buffer) λmax 274 nm (ε8,300) and 311 nm (ε7,580);

IR (KBr) 1744, 1586, 1389, 1353, 1283, 1188, 1160, 1061, 821, 764, and 613 $cm^{-1}$.

EXAMPLE 2

(1S,5R,6S)-2-(2,2-dioxo-2,3-dihydro-2-thia-1-aza-phenylen-1-ylmethyl)-6-[1(R)-hydroxy-ethyl]-1-methyl-carbapen-2-em-3-carboxylate

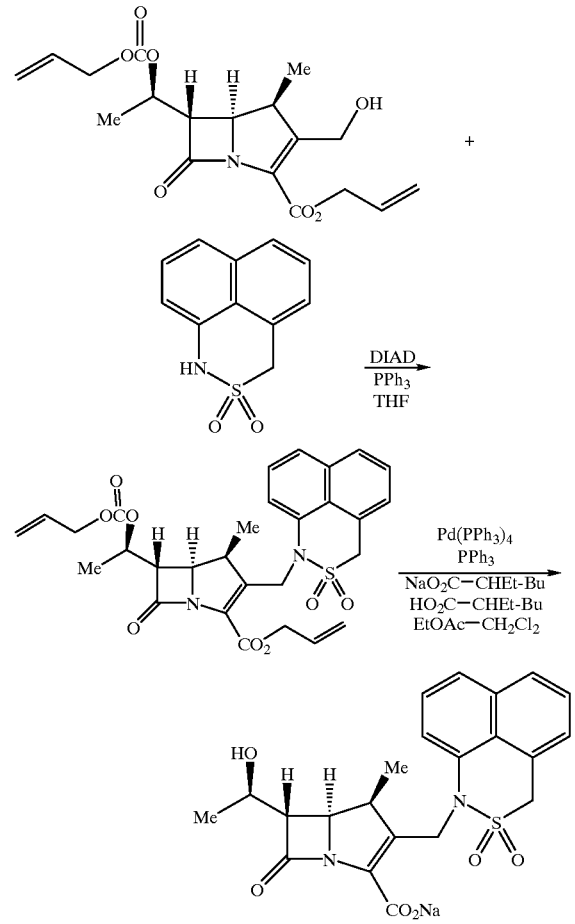

The title compound is prepared according to the procedures of Example 1 by substituting 2,2-dioxo-1H,3H-2-thia-1-aza-phenalene for the 3-methyl-2,2-dioxo-2,3-dihydro-2-thia-1,3-diaza-phenylene in Step 1.

EXAMPLE 3

(1S,5R,6S)-2-{5-[2-(4-carbamoylmethyl-1,4-diazonia-bicyclo[2.2.2]oct-1-yl)-ethyl]-3-methyl-2,2-dioxo-2,3-dihydro-2-thia-1,3-diaza-phenalen-1-ylmethyl}-6-[1(R)-hydroxy-ethyl]-1-methyl-carbapen-2-em-3-carboxylate chloride

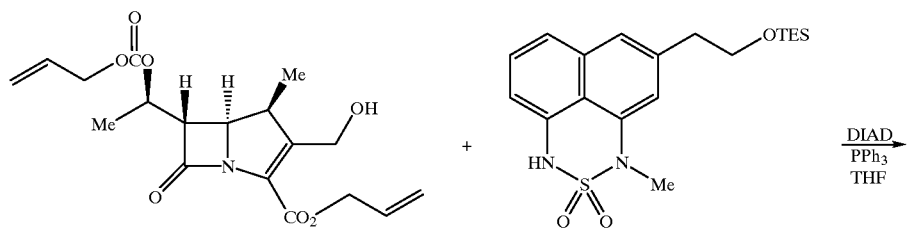

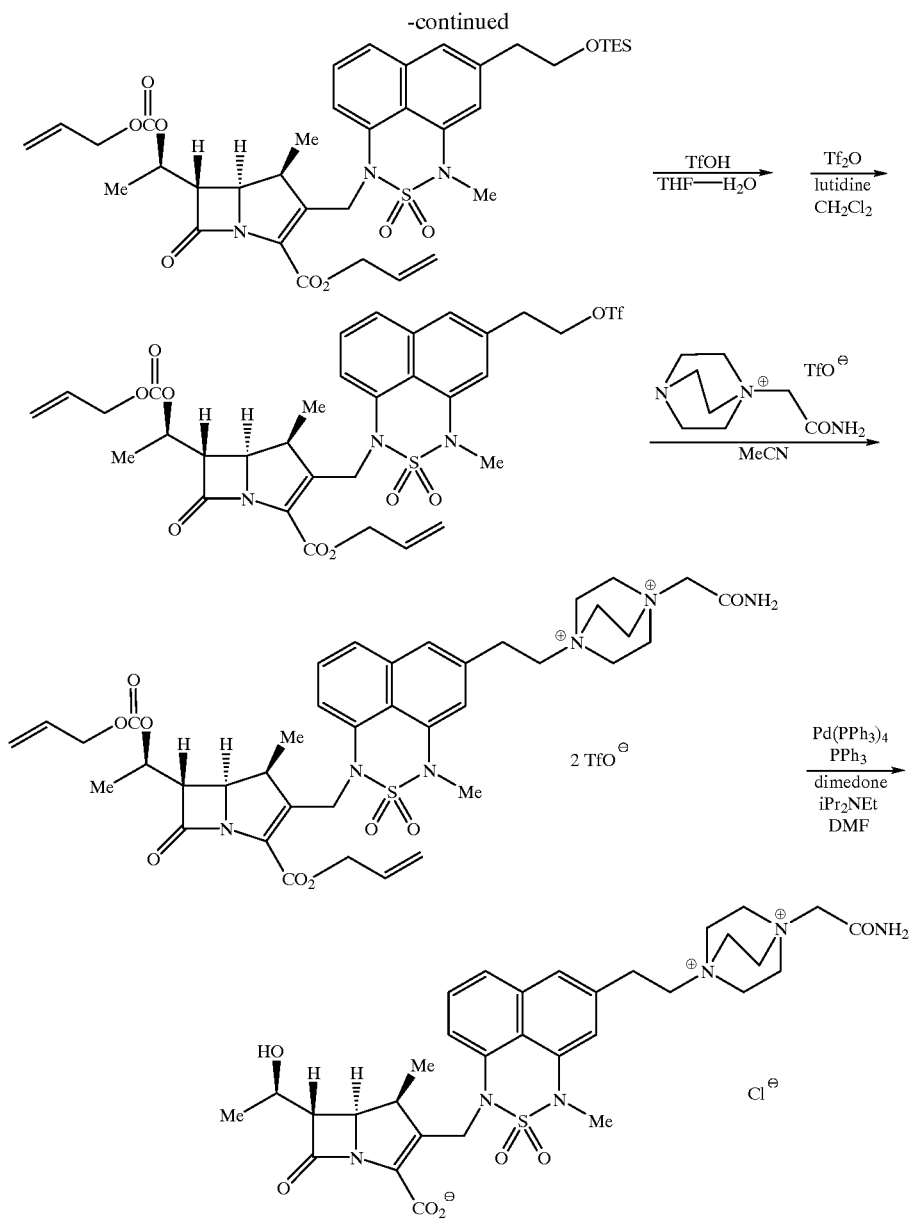

Step 1: Allyl (1S,5R,6S)-6-[1(R)-allyloxycarbonyloxy-ethyl]-1-methyl-2-[3-methyl-2,2-dioxo-5-(2-triethylsilanyloxy-ethyl)-2,3-dihydro-2-thia-1,3-diaza-phenalen-1-ylmethyl]-carbapen-2-em-3-carboxylate A solution of allyl (1S,5R,6S)-6-[1(R)-allyloxycarbonyloxy-ethyl]-2-hydroxymethyl-1-methyl-carbapen-2-em-3-carboxylate (365 mg, 1.0 mmol), triphenylphosphine (315 mg, 1.2 mmol), and 2,2-dioxo-5-(2-triethylsilanyloxy-ethyl)-2,3-dihydro-2-thia-1,3-diaza-phenalene (432 mg, 1.1 mmol) in anhydrous tetrahydrofuran (7 mL) is cooled in an ice-bath and stirred under a nitrogen atmosphere while diisopropyl azodicarboxylate (0.24 mL, 1.2 mmol) is added dropwise over a few minutes. The resulting solution is stirred in the cold for 30 minutes, then diluted with chloroform, washed with 5% aqueous sodium bicarbonate and brine, dried over sodium sulfate, filtered and evaporated under vacuum. The residue is purified by silica gel flash chromatography, eluting with hexane-ethyl acetate, to afford allyl (1S,5R,6S)-6-[1(R)-allyloxycarbonyloxy-ethyl]-1-methyl-2-[3-methyl-2,2-dioxo-5-(2-triethylsilanyloxy-ethyl)-2,3-dihydro-2-thia-1,3-diaza-phenalen-1-ylmethyl]-carbapen-2-em-3-carboxylate.

Step 2: Allyl (1S,5R,6S)-6-[1(R)-allyloxycarbonyloxy-ethyl]-1-methyl-2-{3-methyl-2,2-dioxo-5-[2-(trifluoromethanesulfonyloxy)-ethyl]-2,3-dihydro-2-thia-1,3-diaza-phenalen-1-ylmethyl}-carbapen-2-em-3-carboxylate The compound from step 1 (370 mg, 0.5 mmol) in tetrahydrofuran (4.0 mL) is diluted with water (1.0 mL and treated with 1M aqueous trifluoromethanesulfonic acid (0.05 mL, 0.05 mmol). After stirring at room temperature for 15 minutes, the reaction mixture is partitioned between ethyl acetate (25 mL) and 5% aqueous sodium bicarbonate (5 mL). The organic phase is washed with 50% saturated brine, dried over magnesium sulfate, filtered, evaporated under vacuum, and stripped with anhydrous toluene to leave a residue of the desilylated alcohol.

A solution of the crude alcohol (0.5 mmol) in anhydrous dichloromethane (10 ml) is cooled in an ice-methanol bath (−20° C.) and stirred under a nitrogen atmosphere. The solution is treated with 2,6-lutidine (0.175 mL, 1,5 mmol) followed by trifluoromethanesulfonic anhydride (0.126 mL, 0.75 mmol). After stirring at −20° to −15° C. (bath temperature) for 40 minutes, the solution is diluted with dichloromethane (30 mL), washed with water (20 mL), 0.1N hydrochloric acid (20 mL), and water (20 mL), dried over magnesium sulfate, filtered, and evaporated under vacuum o afford allyl (1S,5R,6S)-6-[1(R)-allyloxycarbonyloxy-ethyl]-1-methyl-2-{3-methyl-2,2-dioxo-5-[2-(trifluoromethanesulfonyloxy)-ethyl]-2,3-dihydro-2-thia-1,3-diaza-phenalen-1-ylmethyl}-carbapen-2-em-3-carboxylate.

Step 3: Allyl (1S,5R,6S)-6-[1(R)-allyloxycarbonyloxy-ethyl]-2-{5-[2-(4-carbamoylmethyl-1,4-diazonia-bicyclo[2.2.2]oct-1-yl)-ethyl]-3-methyl-2,2-dioxo-2,3-dihydro-2-thia-1,3-diaza-phenalen-1-ylmethyl}-1-methylcarbapen-2-em-3-carboxylate bis(trifluoromethanesulfonate)

A sample (95 mg, 0.125 mmol) of the triflate derivative prepared as described in step 2 is dissolved in anhydrous acetonitrile (1.0 mL) and the solution is treated with 1-carbamoylmethyl-1-azonia-4-aza-bicyclo[2.2.2]octane trifluoromethanesulfonate (44 mg, 0.14 mmol). The reaction mixture is stirred at room temperature for 90 minutes, then evaporated under vacuum to a residue which is aged an additional 90 minutes at room temperature. The residue is triturated with anhydrous diethyl ether to afford allyl (1S,5R,6S)-6-[1(R)-allyloxycarbonyloxy-ethyl]-2-{5-[2-(4-carbamoylmethyl-1,4-diazonia-bicyclo[2.2.2]oct-1-yl)-ethyl]-3-methyl-2,2-dioxo-2,3-dihydro-2-thia-1,3-diaza-phenalen-1-ylmethyl}-1-methyl-carbapen-2-em-3-carboxylate bis(trifluoromethanesulfonate).

Step 4: (1S,5R,6S)-2-{5-[2-(4-carbamoylmethyl-1,4-diazonia-bicyclo[2.2.2]oct-1-yl)-ethyl]-3-methyl-2,2-dioxo-2,3-dihydro-2-thia-1,3-diaza-phenalen-1-ylmethyl}-6-[1(R)-hydroxy-ethyl]-1-1-methyl-carbapen-2-em-3-carboxylate chloride The crude bisprotected intermediate of step 3 (approximately 0.125 mmol), triphenylphosphine (4.9 mg, 0.0187 mmol), dimedone (53 mg, 0.378 mmol), and tetrakis(triphenylphosphine)palladium(0) (7.2 mg, 0.0062 mmol) are dissolved in anhydrous dimethylformamide (1.3 mL). The solution is purged with nitrogen, then treated with N,N-diisopropylethylamine (0.065 mL, 0.373 mmol). After stirring at room temperature for 15 minutes, the reaction mixture is added to diethyl ether to precipitate the crude product. The precipitate is triturated with ether (2×5 mL) and dried under vacuum. The precipitate in 1:1 acetonitrile-water (1 mL) is added to a column of Macro-Prep CM (Bio-Rad) weak cation exchange resin (3 mL). The column is successively eluted with 1:1 acetonitrile-water (4 mL), water (3×5 mL), and 5% aqueous sodium chloride (5×3 mL). The product containing sodium chloride fractions are pooled, cooled in ice, and loaded onto a cloumn of Amberchrom CG-161 (TosoHaas) resin (3 mL). The Amberchrom column is eluted with ice-cold water (3×5 mL) followed by 20% isopropanol in water (10×3 mL). The product containing aqueous isopropanol fractions are combined, concentrated under vacuum to remove the isopropanol, and lyophiled to afford the title compound as an amorphous solid.

EXAMPLES 4–38

By appropriately modifying the procedures of Examples 1–3, the following compounds are prepared:

TABLE 2

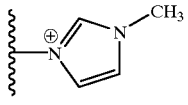

| Ex. | Q—R$^q$ |
|---|---|
| 4 | 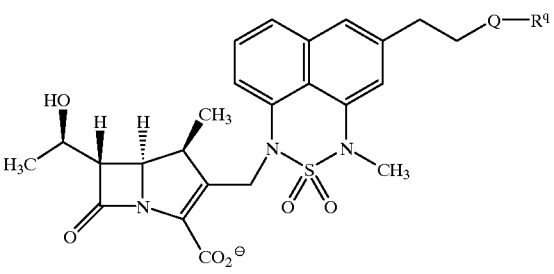 |
| 5 | 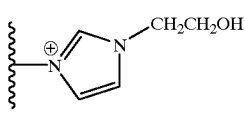 |
| 6 | 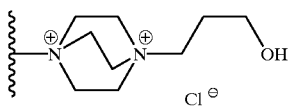 |
| 7 | 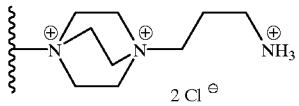 |
| 8 | 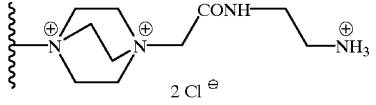 |

TABLE 3

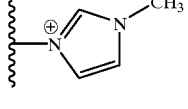

| Ex. | Q—R$^q$ |
|---|---|
| 9 | 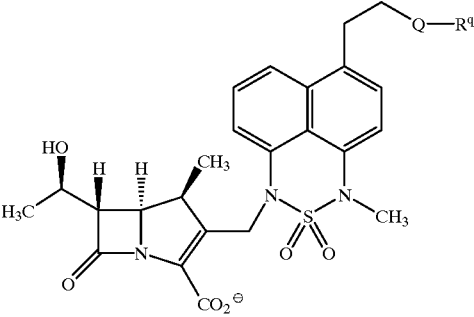 |

TABLE 3-continued
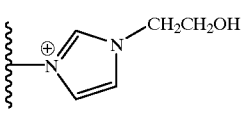
| Ex. | Q—R$^q$ |
|---|---|
| 10 | 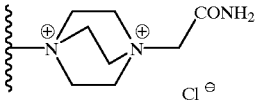 |
| 11 | 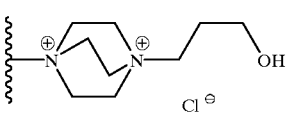 |
| 12 | 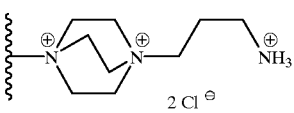 |
| 13 | 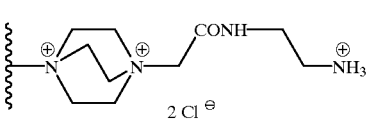 |
| 14 | 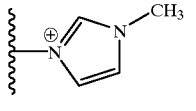 |
TABLE 4
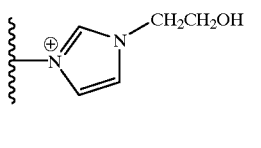
| Ex. | Q—R$^q$ |
|---|---|
| 15 | 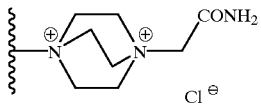 |
| 16 | 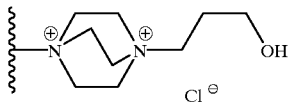 |
| 17 | 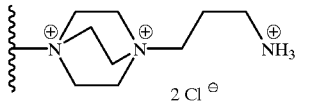 |
| 18 | 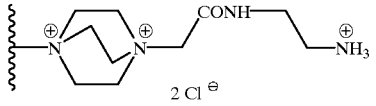 |
| 19 |  |
| 20 |  |

TABLE 5
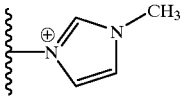
| Ex. | Q—Rq |
|---|---|
| 21 | 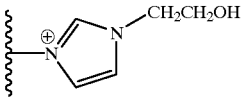 |
| 22 | 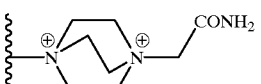 |
| 23 | 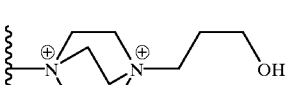 |
| 24 | 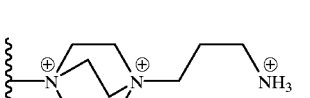 |
| 25 | 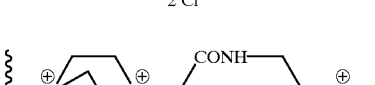 |
| 26 | 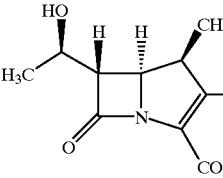 |
TABLE 6
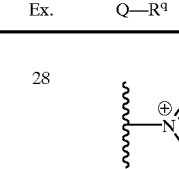
| Ex. | Q—Rq |
|---|---|
| 27 | 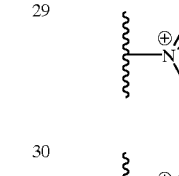 |
TABLE 6-continued
| Ex. | Q—Rq |
|---|---|
| 28 | 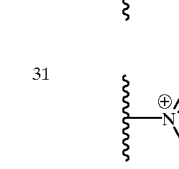 |
| 29 | 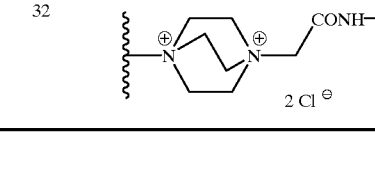 |
| 30 | 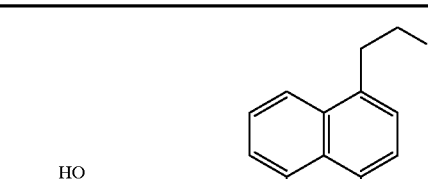 |
| 31 | 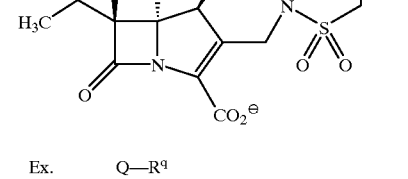 |
| 32 | 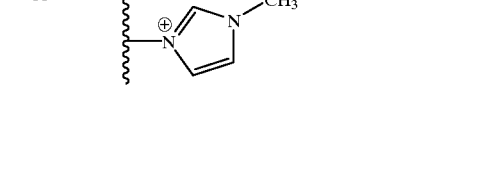 |
TABLE 7
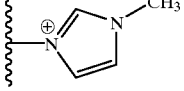
| Ex. | Q—Rq |
|---|---|
| 33 | 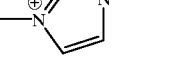 |

TABLE 7-continued

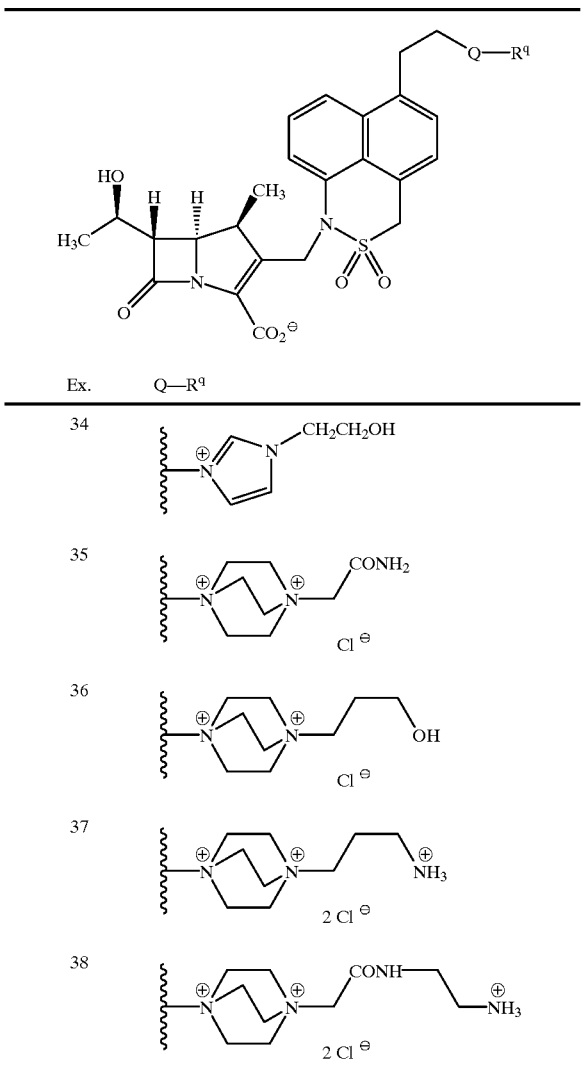

| Ex. | Q—R$^q$ |
|---|---|
| 34 | 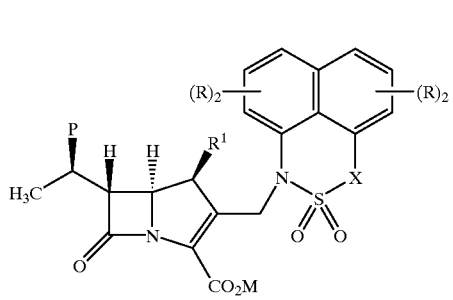 |
| 35 | |
| 36 | |
| 37 | |
| 38 | |

What is claimed is:

1. A compound represented by formula I:

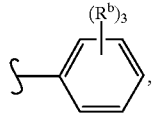

including pharmaceutically acceptable salts thereof, wherein:

$R^1$ represents H or methyl;

$CO_2M$ represents a carboxylic acid, carboxylate anion, or a pharmaceutically acceptable ester group. provided that when $CO_2M$ represents a carboxylate anion it is balanced by Q;

X represents $CR^2R^3$, $NR^2$ or O;

$R^2$ and $R^3$, independently represent H or $C_{1-6}$ alkyl, or $R^2$ and $R^3$ together with the core carbon atom in the group $CR^2R^3$ form a 3–6 membered cycloalkyl ring;

P represents hydrogen, hydroxyl or F;

each R independently represents $R^b$

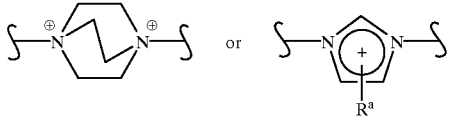

—Het($R^b$)$_3$, $C_{2-6}$ alkenyl, or a group L—Q—$R^q$ with the proviso that only one R group of the type L—Q—$R^q$ can be present;

L is $C_{1-4}$ straight or branched alkylene, uninterrupted, or interrupted by 1–2 of O, S, $NR^a$, C(O), $CO_2$ and C(O)$NR^a$;

Q represents:

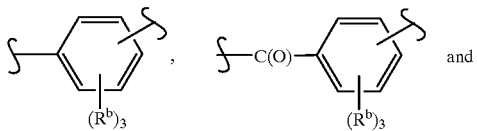

$Y^-$ is a charge balancing group;

n is a value from 1 to 2 selected to maintain overall charge neutrality;

$R^a$ is H or $C_{1-6}$ alkyl;

$R^q$ is $C_{1-6}$ alkyl, straight or branched, uninterrupted or interrupted by 1–2 of O, S, $NR^a$, C(O), C(O)O, C(O)$NR^a$, —CH=CH—, —Het($R^b$)$_3$—, —C(O)Het($R^b$)$_3$—, —C(O)$NR^a$Het($R^b$)$_3$—,

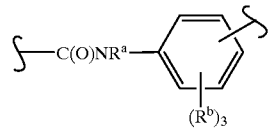

said $R^q$ being unsubstituted or substituted with 1–3 $R^c$ groups;

Het is a heteroaryl group;

each $R^b$ is independently selected from H, halo, $OR^a$, OC(O)$R^a$, C(O)$R^a$, CN, C(O)$NR^aR^d$, $NO_2$, $NR^aR^d$, $SO_2NR^aR^d$ and $C_{1-4}$ alkyl unsubstituted or substituted with 1–3 groups selected from $R^e$;

each $R^c$ is independently selected from halo, $OR^f$, OC(O)$R^f$, $SR^f$, S(O)$R^f$, $SO_2R^f$, CN, C(O)$R^f$, $CO_2R^f$, $NR^fR^g$, $N^+R^aR^fR^gZ^-$, C(O)$NR^aR^f$, —Het($R^b$)$_3$, C(=$N^+R^aR^f$)$R^aZ^-$, C(=$N^+R^aR^f$)$NR^aR^fZ^-$, $NR^aC$(=$N^+R^aR^f$)$R^aZ^-$, $NR^aC$(=$N^+R^aR^f$)$NR^aR^fZ^-$, heteroarylium($R^b$)$_3Z^-$, $SO_2NR^aR^f$, OC(O)$NR^aR^f$, $NR^aC$(O)$R^f$, $NR^aC$(O)$NR^aR^f$, and $R^e$ is selected from halo, $OR^a$, $NR^aR^d$ and $CONR^aR^d$;
$R^f$ is H; $C_{1-6}$ straight or branched chain alkyl, unsubstituted or substituted with 1–3 $R^e$ groups; —Het $(R^b)_3$; $C_{3-6}$ cycloalkyl, unsubstituted or substituted with 1–3 $R^e$ groups, and $R^g$ is H, $C_{1-6}$ alkyl, unsubstituted or substituted with 1–3 $R^e$ groups; $C_{3-6}$ cycloalkyl, unsubstituted or substituted with 1–3 $R^e$ groups; $C(=N^+R^aR^f)R^aZ^-$ or $C(=N^+R^aR^f)NR^aR^fZ^-$, and
$Z^-$ is a charge balancing group $Y^-$.

2. A compound in accordacnce with claim 1 wherein $R^1$ represents methyl.

3. A compound in accordance with claim 1 wherein $CO_2M$ represents a carboxylate anion.

4. A compound in accordance with claim 1 wherein one R represents L—Q—Rq and all other R groups represent H, halo or $C_{1-4}$ alkyl unsubstituted or substituted with 1–3 groups selected from $R^e$.

5. A compound in accordance with claim 4 wherein M represents a negative charge which is balanced by a positively charged Q group.

6. A method of treating a bacterial infection comprising administering to a mammalian patient in need of such treatment a compound as defined in claim 1 in an amount which is effective for treating a bacterial infection.

7. A compound in accordance with claim 4 wherein L represents —$CH_2$— or —$CH_2CH_2$—.

8. A compound in accordance with claim 4 wherein Q represents wherein $Y^-$ represents a charge balancing group, and n is 1 to 2.

9. A compound in accordance with claim 4 wherein $R^q$ is straight or branched $C_{1-6}$ alkyl, substituted with 1–3 $R^c$ groups.

10. A compound in accordance with claim 1 wherein X is $CR^2R^3$.

11. A compound in accordance with claim 1 wherein X is $NR^2$.

12. A compound in accordance with claim 1 wherein X is O.

13. A compound in accordance with claim 1 wherein each R is independently H, halo or $C_{1-4}$ alkyl unsubstituted or substituted with 1–3 groups selected from $R^e$.

14. A compound in accordance with claim 1 wherein:
$R^1$ represents $CH_3$;
$CO_2M$ represents a carboxylate anion;
P represents hydroxyl or hydroxyl protected by a hydroxyl protecting group;
one R is L—Q—$R^q$ and each remaining R is independently H, halo or $C_{1-4}$ alkyl unsubstituted or substituted with 1–3 groups selected from $R^e$;
$R^a$ is H or C16 alkyl;
$R^d$ is H or $C_{1-4}$ alkyl;
$R^e$ is halo, $OR^a$, $NR^aR^d$ or $CONR^aR^d$;
L represents —$CH_2$— or —$CH_2CH_2$—;
Q represents wherein $Y^-$ represents a charge balancing group, n is 1 to 2, and Rq is straight or branched $C_{1-6}$ alkyl, optionally interrupted by $C(O)NR^a$ or and
substituted with 1–3 $R^c$ groups, and $R^c$ is as originally defined.

15. A carbapenem antibacterial compound represented by the formulas in Table 1, wherein three R(s) are H in compounds 4 through 28:

TABLE I

P = H, OH, or F and $R^1$ =H, or Methyl

| X | Substituent(s) R | M |
|---|---|---|
| 1 $NCH_3$ | H | Na |
| 2 $CH_2$ | H | Na |
| 3 O | H | Na |
| 4 $NCH_3$ | 5'-$(CH_2)_n$— imidazole-$CH_3$ | ⊖ |

$n$ = 1,2

TABLE I-continued

[Structure: carbapenem core with P-CH(CH3)- group, R¹ substituent, CO2M group, and CH2-N-S(O2)-X linker to a naphthalene ring system bearing (R)2 substituents at positions 4',5' and 7',8']

P = H, OH, or F and R¹ = H, or Methyl

| # | X | Substituent(s) R | M |
|---|---|---|---|
| 5 | NCH₃ | 6'-(CH₂)ₙ-[N-methylimidazolium], n = 1,2 | ⊖ |
| 6 | CH₂ | 6'-(CH₂)ₙ-[N-methylimidazolium], n = 1,2 | ⊖ |
| 7 | NCH₃ | 6'-(CH₂)ₙ-[N-(CH₂CH₂OH)imidazolium], n = 1,2 | ⊖ |
| 8 | NCH₃ | 4'-(CH₂)ₙ-[DABCO-CH₂CONH₂]⁺ Cl⁻, n = 1,2 | ⊖ |
| 9 | NCH₃ | 5'-(CH₂)ₙ-[DABCO-CH₂CONH₂]⁺ Cl⁻, n = 1,2 | ⊖ |
| 10 | NCH₃ | 6'-(CH₂)ₙ-[DABCO-CH₂CONH₂]⁺ Cl⁻, n = 1,2 | ⊖ |
| 11 | CH₂ | 4'-(CH₂)ₙ-[DABCO-CH₂CONH₂]⁺ Cl⁻, n = 1,2 | ⊖ |
| 12 | CH₂ | 5'-(CH₂)ₙ-[DABCO-CH₂CONH₂]⁺ Cl⁻, n = 1,2 | ⊖ |
| 13 | CH₂ | 6'-(CH₂)ₙ-[DABCO-CH₂CONH₂]⁺ Cl⁻, n = 1,2 | ⊖ |
| 14 | O | 6'-(CH₂)ₙ-[DABCO-CH₂CONH₂]⁺ Cl⁻, n = 1,2 | ⊖ |
| 15 | NCH₂CH₃ | 6'-(CH₂)ₙ-[DABCO-CH₂CONH₂]⁺ Cl⁻, n = 1,2 | ⊖ |
| 16 | CHCH₃ | 6'-(CH₂)ₙ-[DABCO-CH₂CONH₂]⁺ Cl⁻, n = 1,2 | ⊖ |
| 17 | C(CH₃)₂ | 6'-(CH₂)ₙ-[DABCO-CH₂CONH₂]⁺ Cl⁻, n = 1,2 | ⊖ |
| 18 | NCH₃ | 5'-(CH₂)ₙ-[DABCO-(CH₂)₃OH]⁺ Cl⁻, n = 1,2 | ⊖ |
| 19 | NCH₃ | 6'-(CH₂)ₙ-[DABCO-(CH₂)₃OH]⁺ Cl⁻, n = 1,2 | ⊖ |
| 20 | CH₂ | 6'-(CH₂)ₙ-[DABCO-(CH₂)₃OH]⁺ Cl⁻, n = 1,2 | ⊖ |

TABLE I-continued

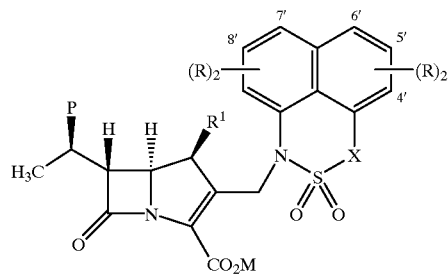

P = H, OH, or F and R¹ =H, or Methyl

| X | Substituent(s) R | M |
|---|---|---|
| 21 NCH₃ | 5'-(CH₂)ₙ-N⊕[DABCO]N⊕-(CH₂)₃NH₃⊕, n = 1,2, 2 Cl⁻ | ⊖ |
| 22 NCH₃ | 6'-(CH₂)ₙ-N⊕[DABCO]N⊕-(CH₂)₃NH₃⊕, n = 1,2, 2 Cl⁻ | ⊖ |
| 23 CH₂ | 6'-(CH₂)ₙ-N⊕[DABCO]N⊕-(CH₂)₃NH₃⊕, n = 1,2, 2 Cl⁻ | ⊖ |
| 24 NCH₃ | 5'-(CH₂)ₙ-N⊕[DABCO]N⊕-CH₂CNH-CH₂CH₂NH₃⊕, n = 1,2, 2 Cl⁻ | ⊖ |
| 25 NCH₃ | 6'-(CH₂)ₙ-N⊕[DABCO]N⊕-CH₂CNH-CH₂CH₂NH₃⊕, n = 1,2, 2 Cl⁻ | ⊖ |
| 26 CH₂ | 6'-(CH₂)ₙ-N⊕[DABCO]N⊕-CH₂CNH-CH₂CH₂NH₃⊕, n = 1,2, 2 Cl⁻ | ⊖ |
| 27 NCH₃ | 7'-Br, 5'-(CH₂)ₙ-N⊕[DABCO]N⊕-CH₂CONH₂, Cl⁻, n = 1,2 | ⊖ |
| 28 NCH₃ | 7'-Cl, 5'-(CH₂)ₙ-N⊕[DABCO]N⊕-CH₂CONH₂, Cl⁻, n = 1,2 | ⊖ |

TABLE I-continued

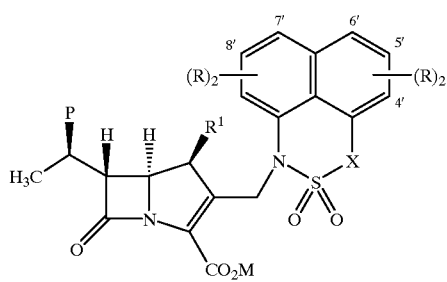

P = H, OH, or F and R¹ =H, or Methyl

| X | Substituent(s) R | M |
|---|---|---|
| 29 NCH₃ | 4'(CH₂)ₙ-N⊕[imidazole]N-CH₃, n = 1, 2 | ⊖ |
| 30 NCH₃ | 4'(CH₂)ₙ-N⊕[imidazole]N-CH₂CH₂OH, n = 1, 2 | ⊖ |
| 31 NCH₃ | 4'(CH₂)ₙ-N⊕[DABCO]N⊕-(CH₂)₃OH, Cl⁻, n = 1, 2 | ⊖ |
| 32 NCH₃ | 4'(CH₂)ₙ-N⊕[DABCO]N⊕-NH₃⊕, 2 Cl⁻, n = 1, 2 | ⊖ |
| 33 NCH₃ | 4'(CH₂)ₙ-N⊕[DABCO]N⊕-CH₂CONH-CH₂-NH₃⊕, 2 Cl⁻, n = 1, 2 | ⊖ |
| 34 CH₂ | 6'(CH₂)ₙ-N⊕[imidazole]N-CH₂CH₂OH, n = 1, 2 | ⊖ |
| 35 NCH₃ | 5'(CH₂)ₙ-N⊕[imidazole]N-CH₂CH₂OH, n = 1, 2. | ⊖ |

16. A pharmaceutical composition comprised of a compound in accordance with claim 1 in combination with a pharmaceutically acceptable carrier.

* * * * *